(12) United States Patent
Lochead et al.

(10) Patent No.: US 7,232,827 B2
(45) Date of Patent: Jun. 19, 2007

(54) HETEROARYL SUBSTITUTED 2-PYRIDINYL AND 2-PYRIMIDINYL-6,7,8,9-TETRAHYDROPYRIMIDO[1,2-A] PYRIMIDIN-4-ONE DERIVATIVES

(75) Inventors: Alistair Lochead, Charenton le Pont (FR); Alain Nedelec, Paris (FR); Mourad Saady, Paris (FR); Philippe Yaiche, Les Lilas (FR)

(73) Assignees: Sanofi-Aventis, Paris (FR); Mitsubishi Pharma Corporation, Osaka (JP)

( * ) Notice: Subject to any disclaimer, the term of this patent is extended or adjusted under 35 U.S.C. 154(b) by 84 days.

(21) Appl. No.: 10/504,677

(22) PCT Filed: Feb. 26, 2003

(86) PCT No.: PCT/EP03/02651

§ 371 (c)(1),
(2), (4) Date: Mar. 24, 2005

(87) PCT Pub. No.: WO03/072579

PCT Pub. Date: Sep. 4, 2003

(65) Prior Publication Data

US 2005/0222172 A1    Oct. 6, 2005

(30) Foreign Application Priority Data

Feb. 28, 2002 (EP) .................................. 02290485
Feb. 28, 2002 (EP) .................................. 02290486

(51) Int. Cl.
*A01N 43/90* (2006.01)
*A61K 31/519* (2006.01)
*C07D 471/00* (2006.01)
*C07D 487/00* (2006.01)

(52) U.S. Cl. ............................. 514/259.1; 514/259.4; 514/259.41; 544/279; 544/280; 544/281

(58) Field of Classification Search ............... 544/281, 544/279, 280; 514/295.5, 259.1, 259.4, 259.41
See application file for complete search history.

(56) References Cited

FOREIGN PATENT DOCUMENTS

WO    WO00/18758    4/2000
WO    WO02/18386    3/2002

OTHER PUBLICATIONS

Leclerc, et al. ("Indirubins Inhibit Glycogen Synthase Kinase-3β and CDK5/P25, Two Protein Kinases Involved in Abnormal Tau Phosphorylation in Alzheimer's Disease," The Journal of Biological Chemistry, 276, No. 1, Jan. 2, 2001, pp. 251-260).*
Bhat, et al. ("Glycogen Synthase Kinase 3: A Drug Target for CNS Therapies," Journal of Neurochemistry, 2004, 89, 1313-1317).*
Souillac, et al., Characterization of Delivery Systems, Differential Scanning Calorimetry, pp. 217-221 (in Encyclopedia of Controlled Drug Delivery, 1999, John Wiley & Sons, pp. 212-227).*
Wagman, et al., Discovery and Development of GSK3 Inhibitors for the Treatment of Type 2 Diabetes, Current Pharmaceutical Design, 2004, 10, 1105-1137.*
Disorders Index of the National Institute of Neurological Disorders and Stroke, Oct. 2006 http://www.ninds.nih.gov/disorders/disorder_index.htm?css=print.*
Harwood, (PubMed abstract of Curr. Mol. Med., Aug. 2003; 3(5): 472-82).*

* cited by examiner

*Primary Examiner*—Deepak Rao
*Assistant Examiner*—Cecilia Jaisle
(74) *Attorney, Agent, or Firm*—Balaram Gupta

(57) ABSTRACT

The invention relates to a pyrimidone derivative represented by formula (I) or a salt thereof wherein: (I) X represents two hydrogen atoms, a sulphur atom, an oxygen atom or a $C_{1-2}$ alkyl group and a hydrogen atom; Y represents a bond, an ethenylene group, an ethynylene group or a methylene group optionally substituted; R1 represents a 2, 3 or 4-pyridine ring or a 2, 4 or 5-pyrimidine ring optionally substituted; R2 represents a heterocyclic bicyclic rings, having 1–4 heteroatoms selected from an oxygen atom, a sulfur atom and a nitrogen atom and having 5–9 carbon atoms, of formula (II) R3 represents a hydrogen atom, a $C_{1-6}$ alkyl group, a hydroxy group, a $C_{1-4}$ alkoxy group or a halogen atom; R4 represents a hydrogen atom, a $C_{1-6}$ alkyl group, a $C_{1-4}$ alkoxy group or a halogen atom. The invention relates also to a medicament comprising the said derivative or a salt thereof as an active ingredient which is used for preventive and/or therapeutic treatment of a neurodegenerative disease caused by abnormal activity of GSK3β or GSK3β and cdk5/p25, such as Alzheimer disease

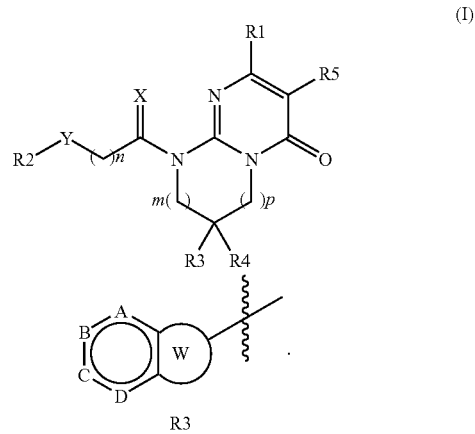

12 Claims, No Drawings

HETEROARYL SUBSTITUTED 2-PYRIDINYL AND 2-PYRIMIDINYL-6,7,8,9-TETRAHYDROPYRIMIDO[1,2-A] PYRIMIDIN-4-ONE DERIVATIVES

TECHNICAL FIELD

The present invention relates to compounds that are useful as an active ingredient of a medicament for preventive and/or therapeutic treatment of neurodegenerative diseases caused by abnormal activities of GSK3β alone or by the combined effects of GSK3β and cdk5/p25.

BACKGROUND ART

GSK3β (glycogen synthase kinase 3β) is a proline directed serine, threonine kinase that plays an important role in the control of metabolism, differentiation and survival. It was initially identified as an enzyme able to phosphorylate and hence inhibit glycogen synthase. It was later recognised that GSK3β was identical to tau protein kinase 1 (TPK1), an enzyme that phosphorylates tau protein in epitopes that are also found to be hyperphosphorylated in Alzheimer's disease and in several tauopathies.

Interestingly, protein kinase B (AKT) phosphorylation of GSK3β results in a loss of its kinase activity, and it has been hypothesised that this inhibition may mediate some of the effects of neurotrophic factors. Moreover, phosphorylation by GSK3, of β-catenin, a protein involved in cell survival, results in its degradation by an ubiquitinilation dependent proteasome pathway.

Thus, it appears that inhibition of GSK3β activity may result in neurotrophic activity. Indeed there is evidence that lithium, an non-competitive inhibitor of GSK3β, enhances neuritogenesis in some models and also increases neuronal survival, through the induction of survival factors such as Bcl-2 and the inhibition of the expression of proapoptotic factors such as P53 and Bax.

Recent studies have demonstrated that β-amyloid increases the GSK3β activity and tau protein phosphorylation. Moreover, this hyperphosphorylation as well as the neurotoxic effects of β-amyloid are blocked by lithium chloride and by a GSK3β antisense mRNA. These observations strongly suggest that GSK3β may be the link between the two major pathological processes in Alzheimer's disease: abnormal APP (Amyloid Precursor Protein) processing and tau protein hyperphosphorylation.

Although tau hyperphosphorylation results in a destabilisation of the neuronal cytoskeleton, the pathological consequences of abnormal GSK3β activity are, most likely, not only due to a pathological phosphorylation of tau protein because, as mentioned above, an excessive activity of this kinase may affect survival through the modulation of the expression of apoptotic and antiapoptotic factors. Moreover, it has been shown that β-amyloid-induced increase in GSK3β activity results in the phosphorylation and, hence the inhibition of pyruvate dehydrogenase, a pivotal enzyme in energy production and acetylcholine synthesis.

Cdk5/p25, also known as tau protein kinase 2 (TPK2), is a proline directed, Ser/Thr kinase essential for central nervous system development and in particular for neuronal migration and neurite outgrowth. Cdk5 is a homologue of cyclin-dependent kinases and rather ubiquitously expressed. Its activator p35 (a 305 aa protein) or a truncated form p25 (208 aa, missing an N-terminal proline-rich domain not required for activity) are selectively expressed in neurons, limiting cdk5 kinase activity essentially to the CNS. Cdk5 is completely inactive in the absence of p35 or p25. The term cdk5/p25 will be used here for the active enzyme since evidence exists suggesting that p25 and less so p35 may be involved in pathological processes.

Physiological substrates of cdk5/p25 include DARPP-32, Munc-18, PAK1, synapsin 1 and perhaps some others. In addition, it is now well established that cdk5/p25 phosphorylates tau protein epitopes which are hyperphosphorylated in Alzheimer's disease. More recently, elevated cdk5/p25 activity, mislocalization of cdk5 and an increase in p25 activator has been found in the brain of Alzheimer patients. Interestingly, prephosphorylation of tau protein by cdk5/p25 considerably enhances phosphorylation of tau by GSK3β on other epitopes, also found hyperphosphorylated in Alzheimer's disease. Moreover, neurofibrillary tangles, the hallmark of Alzheimer's disease, are labelled with antisera for GSK3β and cdk5, but not GSK3α and MAP kinase, also, GSK3β and cdk5 are associated with microtubules and both, more than PKA and CK, contribute to the AD-like phosphorylation of tau protein. These results taken together suggest that mixed inhibitors of GSK3β and cdk5/p25 should efficient in protecting tau protein from hyperphosphorylation. Therefore, they would be useful in the treatment of any pathological disorder associated with the abnormal phosphorylaton of tau protein, in particular Alzheimer's disease, but also other tauopathies (e.g. frontotemporoparietal dementia, corticobasal degeneration, Pick's disease, progressive supranuclear palsy).

Cdk5/p25 has been linked to apoptosis and neurodegeneration in more general terms. Its overexpression induces apoptosis in cultured neurons, in brain tissue apoptotic cells show strong immunoreactivity for cdk5. Neurotoxic agents, incl. Aβ(1-42), neuronal injury, ischemia or growth factor withdrawal lead to activation and mislocalization of cdk5/p25, abnormal phosphorylation of cdk5 substrates, cytoskeletal disruption and cell death. Moreover, phosphorylation by cdk5/p25 transforms DARPP-32 into an inhibitor of protein kinase A, reducing signal transduction in the striatum with obvious implications for Parkinson's disease. A role for cdk5 in ALS has also been proposed based on its ability to phosphorylate neurofilaments. More recently, deregulation of cdk5 was detected in a mouse model of amyotrophic lateral sclerosis.

Altogether, these experimental observations indicate that GSK3β inhibitors may find application in the treatment of the neuropathological consequences and the cognitive and attention deficits associated with Alzheimer's disease, as well as other acute and chronic neurodegenerative diseases. These include, in a non-limiting manner, Parkinson's disease, tauopathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma.

In addition GSK3β inhibition may find application in the treatment of other diseases such as:

Non-insulin dependent diabetes (such as diabetes type II) and obesity; manic depressive illness; schizophrenia; alopecia; cancers such as breast cancer, non-small cell lung carcinoma, thyroid cancer, T or B-cell leukemia and several virus-induced tumors.

Since it appears that both, GSK3β and cdk5/p25 play a major role in the induction of apoptosis in neuronal cells, combined inhibition of these two enzymes may find application in the treatment of not only Alzheimer's disease and the other above-mentioned tauopathies, but also in a number of other neurodegenerative disorders, in particular Parkinson's disease and amyotrophic lateral sclerosis; other dementias including vascular dementia; acute stroke and other traumatic injuries; cerebrovascular accidents (e.g. age related macular degeneration); brain and spinal cord trauma; peripheral neuropathies; retinopathies and glaucoma.

In addition mixed TPK1/TPK2 inhibitors may find their applications in the treatment of other diseases such as: smoking cessation and other withdrawal syndromes, epilepsy.

DISCLOSURE OF THE INVENTION

An object of the present invention is to provide compounds useful as an active ingredient of a medicament for preventive and/or therapeutic treatment of a disease caused by abnormal GSK3β or GSK3β and cdk5/p25 activity, more particularly of neurodegenerative diseases. More specifically, the object is to provide novel compounds useful as an active ingredient of a medicament that enables prevention and/or treatment of neurodegenerative diseases such as Alzheimer's disease.

Thus, the inventors of the present invention have identified compounds possessing inhibitory activity against GSK3β. As a result, they found that compounds represented by the following formula (I) had the desired activity and were useful as an active ingredient of a medicament for preventive and/or therapeutic treatment of the aforementioned diseases.

The present invention thus provides pyrimidone derivatives represented by formula (I) or salts thereof, solvates thereof or hydrates thereof:

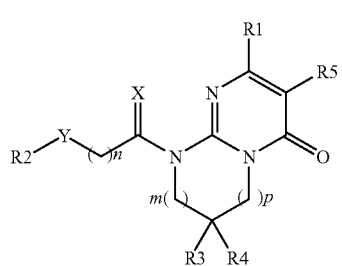

wherein:

X represents two hydrogen atoms, a sulphur atom, an oxygen atom or a $C_{1-2}$ alkyl group and a hydrogen atom;

Y represents a bond, an ethenylene group, an ethynylene group or a methylene group optionally substituted by one or two groups chosen from a $C_{1-6}$ alkyl group, a hydroxy group or a $C_{1-4}$ alkoxy group;

R1 represents a 2, 3 or 4-pyridine ring or a 2, 4 or 5-pyrimidine ring, the ring being optionally substituted by a $C_{3-6}$ cycloalkyl group, a $C_{1-4}$ alkyl group, a $C_{1-4}$ alkoxy group, a benzyl group or a halogen atom;

R2 represents a heterocyclic bicyclic rings, having 1–4 heteroatoms selected from an oxygen atom, a sulfur atom and a nitrogen atom and having 5–9 carbon atoms, of formula

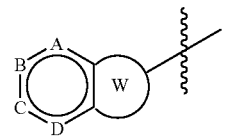

wherein A, B, C and D represent, each independently, a carbon atom or a nitrogen atom and W represent a saturated or unsaturated 5, 6 or 7 membered cyclic ring having from 3 to 7 carbon atoms and 2 to 0 heteroatoms such as an oxygen atom, a sulfur atom or a nitrogen atom; the R2 group being optionally substituted on a carbon atom or, when possible, on a nitrogen atom by one or two atoms or groups chosen from a halogen atom, a $C_{1-6}$ alkyl group, a hydroxy group, a $C_{1-4}$ alkoxy group, a phenyl ring, a pyridine ring or a —NR6R7 group;

R3 represents a hydrogen atom, a $C_{1-6}$ alkyl group, a hydroxy group, a $C_{1-4}$ alkoxy group or a halogen atom;

R4 represents a hydrogen atom, a $C_{1-6}$ alkyl group, a $C_{1-4}$ alkoxy group or a halogen atom;

R5 represents a hydrogen atom, a $C_{1-6}$ alkyl group, a $C_{1-2}$ perhalogenated alkyl group, a $C_{1-3}$ halogenated alkyl group or a halogen atom;

R6 and R7 represent, each independently, a hydrogen atom, a $C_{1-6}$ alkyl group, a benzyl group, a phenyl ring or R6 and R7 represent together with the nitrogen atom, a pyrrolidine ring, a piperidine ring, a hexamethyleneimine ring, a morpholine ring or a piperazine ring, the rings being optionally substituted by one or two $C_{1-6}$ alkyl group;

When m equals 0, p equals 1, 2 or 3,
When m equals 1, p equals 0, 1 or 2,
When m equals 2, p equals 0 or 1;
When m equals 3, p equals 0;
and
n represents 0 to 3;

with the proviso that the derivative of formula (I) is not:
9-[2-(1H-indol-3-yl)ethyl]-2-pyridin-4-yl-6,7,8,9-tetrahydro-4H-pyrimido[1,2-a]pyrimidin-4-one;
9-[3-(1H-indol-3-yl)propyl]-2-pyridin-4-yl-6,7,8,9-tetrahydro-4H-pyrimido[1,2-a]pyrimidin-4-one;
1-[2-(1H-Indol-3-yl)ethyl]-7-pyridin-4-yl-2,3-dihydroimidazo[1,2-a]pyrimidin-5(1H)-one, or
1-[3-(1H-indol-3-yl)propyl]-7-pyridin-4-yl-2,3-dihydroimidazo[1,2-a]pyrimidin-5(1H)-one.

According to another aspect of the present invention, there is provided a medicament comprising as an active ingredient a substance selected from the group consisting of the pyrimidone derivatives represented by formula (I) and the physiologically acceptable salts thereof, and the solvates thereof and the hydrates thereof. As preferred embodiments of the medicament, there are provided the aforementioned medicament which is used for preventive and/or therapeutic treatment of diseases caused by abnormal GSK3β or GSK3β and cdk5/p25 activity, and the aforementioned medicament which is used for preventive and/or therapeutic treatment of neurodegenerative diseases and in addition other diseases such as:

Non-insulin dependent diabetes (such as diabetes type II) and obesity; manic depressive illness; schizophrenia; alopecia; smoking cessation and other withdrawal syndromes, epilepsy; cancers such as breast cancer, non-small cell lung carcinoma, thyroid cancer, T or B-cell leukemia and several virus-induced tumors.

As further preferred embodiments of the present invention, there are provided the aforementioned medicament wherein the diseases are neurodegenerative diseases and are selected from the group consisting of Alzheimer's disease, Parkinson's disease, amyotrophic lateral sclerosis, tauopathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma, and the aforementioned medicament in the form of pharmaceutical composition containing the above substance as an active ingredient together with one or more pharmaceutical additives.

The present invention further provides an inhibitor of GSK3β or GSK3β and cdk5/p25 activity comprising as an active ingredient a substance selected from the group consisting of the pyrimidone derivatives of formula (I) and the salts thereof, and the solvates thereof and the hydrates thereof.

According to further aspects of the present invention, there is provided a method for preventive and/or therapeutic treatment of neurodegenerative diseases caused by abnormal GSK3β or GSK3β and cdk5/p25 activity, which comprises the step of administering to a patient a preventively and/or therapeutically effective amount of a substance selected from the group consisting of the pyrimidone derivatives of formula (I) and the physiologically acceptable salts thereof, and the solvates thereof and the hydrates thereof; and a use of a substance selected from the group consisting of the pyrimidone derivatives of formula (I) and the physiologically acceptable salts thereof, and the solvates thereof and the hydrates thereof for the manufacture of the aforementioned medicament.

As used herein, the $C_{1-6}$ alkyl group represents a straight or branched alkyl group having 1 to 6 carbon atoms, for example, methyl group, ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, isohexyl group, and the like;

The ethenylene group represents the divalent group of formula:

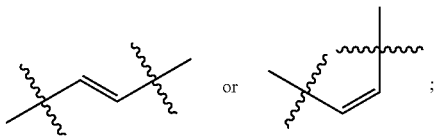

The ethynylene group represents the divalent group of formula:

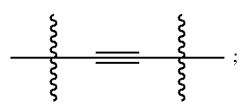

The $C_{1-4}$ alkoxy group represents an alkyloxy group having 1 to 4 carbon atoms for example, methoxy group, ethoxy group, propoxy group, isopropoxy group, butoxy group, isobutoxy group, sec-butoxy group, tert-butoxy group, and the like;

The $C_{1-2}$ perhalogenated alkyl group represents an alkyl group wherein all the hydrogen have been substituted by a halogen atom, for example a $CF_3$ or $C_2F_5$;

The $C_{1-3}$ halogenated alkyl group represents an alkyl group wherein at least one hydrogen has not been substituted by a halogen atom;

The halogen atom represents a fluorine, chlorine, bromine or iodine atom.

The leaving group represents a group which could be easily cleaved and substituted, such a group may be for example a tosyloxy, a mesyloxy, a bromide and the like.

The compounds represented by the aforementioned formula (I) may form a salt. Examples of the salt include, when an acidic group exists, salts of alkali metals and alkaline earth metals such as lithium, sodium, potassium, magnesium, and calcium; salts of ammonia and amines such as methylamine, dimethylamine, trimethylamine, dicyclohexylamine, tris(hydroxymethyl)aminomethane, N,N-bis(hydroxyethyl)piperazine, 2-amino-2-methyl-1-propanol, ethanolamine, N-methylglucamine, and L-glucamine; or salts with basic amino acids such as lysine, δ-hydroxylysine, and arginine. The base-addition salts of acidic compounds are prepared by standard procedures well known in the art.

When a basic group exists, examples include salts with mineral acids such as hydrochloric acid, hydrobromic acid, sulfuric acid, nitric acid, phosphoric acid; salts with organic acids such as methanesulfonic acid, benzenesulfonic acid, p-toluenesulfonic acid, acetic acid, propionic acid, tartaric acid, fumaric acid, maleic acid, malic acid, oxalic acid, succinic acid, citric acid, benzoic acid, mandelic acid, cinnamic acid, lactic acid, glycolic acid, glucuronic acid, ascorbic acid, nicotinic acid, and salicylic acid; or salts with acidic amino acids such as aspartic acid, and glutamic acid.

The acid-addition salts of the basic compounds are prepared by standard procedures well know in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not compromised by side effects ascribable to the anions. Although medicinally acceptable salts of the basic compounds are preferred, all acid-addition salts are within the scope of the present invention.

In addition to the pyrimidone derivatives represented by the aforementioned formula (I) and salts thereof, their solvates and hydrates also fall within the scope of the present invention. The pyrimidone derivatives represented by the aforementioned formula (I) may have one or more asymmetric carbon atoms. As for the stereochemistry of such asymmetric carbon atoms, they may independently be in either (R) and (S) configuration, and the pyrimidone derivative may exist as stereoisomers such as optical isomers, or diastereoisomers. Any stereoisomers in pure form, any mixtures of stereoisomers, racemates and the like fall within the scope of the present invention.

Examples of preferred compounds of the present invention are shown in table 1A, 2A, 1B and 2B hereinafter. However, the scope of the present invention is not limited by these compounds.

Preferred compounds of the present invention represented by formula (I) include also compounds wherein:

(1) R1 represents a 3- or 4-pyridine ring and more preferably 4-pyridine ring or a 4- or 5-pyrimidine ring and more preferably 4-pyrimidine ring, which may be substituted by a $C_{1-2}$ alkyl group, a $C_{1-2}$ alkoxy group or a halogen atom; and/or (2) X represents two hydrogen atoms, an oxygen atom or a $C_{1-2}$ alkyl group and a hydrogen atom;

(3) Y represents a bond or a methylene group optionally substituted by one or two groups chosen from a $C_{1-3}$ alkyl group or a hydroxy group; and/or (4) R2 represents a heterocyclic bicyclic rings, having 1-4 heteroatoms selected from an oxygen atom, a sulfur atom and a nitrogen atom and having 5-9 carbon atoms, of formula

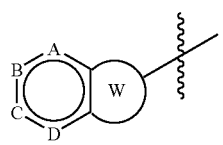

wherein A, B, C and D represent, each independently, a carbon atom or a nitrogen atom and W represent a saturated or unsaturated 5, 6 or 7 membered cyclic ring having from 3 to 7 carbon atoms and 2 to 0 heteroatoms such as an oxygen atom, a sulfur atom or a nitrogen atom; the R2 group being optionally substituted on a carbon atom or, when possible, on a nitrogen atom by one or two atoms or groups chosen from a halogen atom, a $C_{1-6}$ alkyl group, a hydroxy group, a $C_{1-4}$ alkoxy group, a phenyl ring, a pyridine ring or a —NR6R7 group; with the proviso that when R1 is a pyridine ring and R2 is an indole ring; R3, R4 and R5 does not represent a hydrogen atom and (m+p) is different of 1 or 2.

More preferred compounds of the present invention represented by formula (I) include also compounds wherein:

(1) R1 represents an unsubstituted 4-pyridine ring or a 4-pyrimidine ring; and/or (2) X represents two hydrogen atoms; and/or (3) Y represents a bond; and/or (4) R3 and R4 represent each independently a hydrogen atom, a halogen atom or a $C_{1-2}$ alkyl group; and/or (5)
R2 is a heterocyclic bicyclic ring of formula

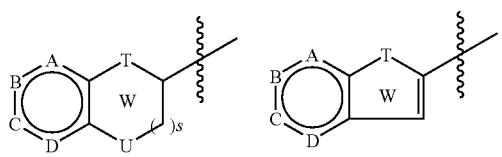

wherein A, B, C and D represent, each independently, a carbon atom or a nitrogen atom and T and U represent, each independently, a carbon atom or a heteroatom such as an oxygen atom, a sulfur atom or a nitrogen atom and s is 0 or 1; or R2 is a heterocyclic bicyclic ring of formula

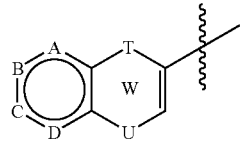

wherein A, B, C and D represent, each independently, a carbon atom or a nitrogen atom and T and U represent, each independently, a carbon atom or a heteroatom such as an oxygen atom or a sulfur atom; or The heterocyclic ring represented by R2 is a heterocyclic bicyclic ring of formula

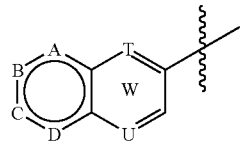

wherein A, B, C and D represent, each independently, a carbon atom or a nitrogen atom and T and U represent, each independently, a carbon atom or a heteroatom such as a nitrogen atom with the proviso that when R1 is a pyridine ring and R2 is an indole ring; R3, R4 and R5 does not represent a hydrogen atom and (m+p) is different of 1 or 2; preferably R2 represents a cyclopentapyrazin; 6,7-dihydro-cyclopentapyrazin; benzofuran, 2,3-dihydrobenzofuran; 1,4-benzodioxan; 2,3-dihydro-benzo[1,4]dioxin; chromane; isochromane; quinoxaline; quinazoline; furopyridine; pyrindine or 6,7-dihydropyrindine group; preferably a 6,7-dihydrocyclopentapyrazin, 6,7-dihydropyrindine, benzofuran, 2,3-dihydrobenzofuran, chromane, 2,3-dihydro-benzo[1,4]dioxin or furopyridine group; and more preferably compounds wherein R1 and X and Y and R3 and R4 and R2 are defined as above.

Particularly preferred compounds of the present invention represented by formula (I), wherein R1 is a pyridine ring, include compounds of table 1A:

N° 1. (+)-(6R)-9-(6,7-Dihydro-5H-[1]pyrindin-6-ylmethyl)-7,7-dimethyl-2-(pyridin-4-yl)-6,7,8,9-tetrahydro-pyrimido[1,2-a]pyrimidin-4-one N° 2. (−)-(6S)-9-(6,7-Dihydro-5H-[1]pyrindin-6-ylmethyl)-7,7-dimethyl-2-(pyridin-4-yl)-6,7,8,9-tetrahydro-pyrimido[1,2-a]pyrimidin-4-one N° 3. (+)-(6R)-9-(6,7-Dihydro-5H-[1]pyrindin-6-ylmethyl)-2-(pyridin-4-yl) -6,7,8,9-tetrahydro-pyrimido[1,2-a]pyrimidin-4-one N° 4. (+/−)-7,7-Dimethyl-9-(2-methyl-6,7-dihydro-5H-[1]pyrindin-6-ylmethyl) -2-(pyridin-4-yl)-6,7,8,9-tetrahydro-pyrimido[1,2-a]pyrimidin-4-one.

N° 5. (+)-7,7-Dimethyl-9-(2-methyl-6,7-dihydro-5H-[1]pyrindin-6-ylmethyl)-2-(pyridin-4-yl)-6,7,8,9-tetrahydro-pyrimido[1,2-a]pyrimidin-4-one N° 6. (−)-7,7-Dimethyl-9-(2-methyl-6,7-dihydro-5H-[1]pyrindin-6-ylmethyl)-2-(pyridin-4-yl)-6,7,8,9-tetrahydro-pyrimido[1,2-a]pyrimidin-4-one N° 7. (+/−)-9-(2,3-Dihydro-benzofuran-2-ylmethyl)-7,7-dimethyl-2-(pyridin-4-yl)-6,7,8,9-tetrahydro-pyrimido[1,2-a]pyrimidin-4-one N° 8. 9-(Furo[3,2-b]pyridin-2-ylmethyl)-7,7-dimethyl-2-(pyridin-4-yl)-6,7,8,9-tetrahydro-pyrimido[1,2-a]pyrimidin-4-one N° 9. 9-(Benzofuran-2-ylmethyl)-7,7-dimethyl-2-(pyridin-4-yl)-6,7,8,9-tetrahydro-pyrimido[1,2-a]pyrimidin-4-one N° 10. (+/−)9-(2-Chloro-6,7-dihydro-5H-[1]pyrindin-6-ylmethyl)-7,7-dimethyl -2-(pyridin-4-yl)-6,7,8,9-tetrahydro-pyrimido[1,2-a]pyrimidin-4-one N° 11. (+/−)7,7-Dimethyl-2-(pyridin-4-yl)-9-[2-(pyridin-4-yl)-6,7-dihydro-5H-[1]pyrindin-6-ylmethyl]-6,7,8,9-tetrahydro-pyrimido[1,2-a]pyrimidine-4-one N° 12. (+/−)7,7-Dimethyl-9-(2-phenyl-6,7-dihydro-5H-[1]pyrindin-6-ylmethyl)-2-(pyridin-4-yl)-6,7,8,9-tetrahydro-pyrimido[1,2-a]pyrimidine-4-one N° 13. (+/−)7,7-Dimethyl-2-(pyridin-4-yl)-9-[2-(pyrrolidin-1-yl)-6,7-dihydro -5H-[1]pyrindin-6-ylmethyl]-6,7,8,9-tetrahydro-pyrimido[1,2-a]pyrimidin-4-one N° 14. (+/−)7,7-Difluoro-9-(2-methyl-6,7-dihydro-5H-[1]pyrindin-6-ylmethyl) -2-(pyridin-4-yl)-6,7,8,9-tetrahydro-pyrimido[1,2-a]pyrimidine-4-one N° 15. 9-((+)-(6-R)-6,7-Dihydro-5H-[1]pyrindin-6-ylmethyl)-(+/−)-7-methyl-2-(pyridin-4-yl)-6,7,8,9-tetrahydro-pyrimido[1,2-a]pyrimidine-4-one.

Particularly preferred compounds of the present invention represented by formula (I), wherein R1 is a pyridine ring, include also compounds of table 2A:

N° 1. 9-Chroman-2-ylmethyl-8-methyl-2-pyridin-4-yl-6,7,8,9-tetrahydro-pyrimido[1,2-a]pyrimidin-4-one N° 2. 9-(8-Methoxy-2,3-dihydro-benzo[1,4]dioxin-2-ylmethyl)-8-methyl-2-pyridin-4-yl-6,7,8,9-tetrahydro-pyrimido[1,2-a]pyrimidin-4-one N° 3. 9-(2,3-Dihydro-benzo[1,4]dioxin-2-ylmethyl)-8-methyl-2-pyridin-4-yl -6,7,8,9-tetrahydro-pyrimido[1,2-a]pyrimidin-4-one N° 4. 9-(5-Methoxy-2,3-dihydro-benzo[1,4]dioxin-2-ylmethyl)-8-methyl-2-pyridin-4-yl-6,7,8,9-tetrahydro-pyrimido[1,2-a]pyrimidin-4-one N° 5. 9-(6,7-Dihydro-5H-[1]pyrindin-6-(R)-ylmethyl)-8,8-dimethyl-2-pyridin-4-yl-6,7,8,9-tetrahydro-pyrimido[1,2-a]pyrimidin-4-one N° 6. 9-Chroman-2-ylmethyl-8,8-dimethyl-2-pyridin-4-yl-6,7,8,9-tetrahydro-pyrimido[1,2-a]pyrimidin-4-one N° 7. 9-(2,3-Dihydro-benzo[1,4]dioxin-2-ylmethyl)-8,8-dimethyl-2-pyridin-4-yl-6,7,8,9-tetrahydro-pyrimido[1,2-a]pyrimidin-4-one N° 8. 9-(8-Fluoro-5-methoxy-chroman-3-ylmethyl)-8,8-dimethyl-2-pyridin-4-yl-6,7,8,9-tetrahydro-pyrimido[1,2-a]pyrimidin-4-one N° 9. 9-Furo[3,2-b]pyridin-2-ylmethyl-8-methyl-2-pyridin-4-yl-6,7,8,9-tetrahydro-pyrimido[[1,2-a]pyrimidin-4-one N° 10. 9-(6,7-Dihydro-5H-[1]pyrindin-6-(R)-ylmethyl)-8-methyl-2-pyridin-4-yl-6,7,8,9-tetrahydro-pyrimido[1,2-a]pyrimidin-4-one N° 11. 9-(6,7-Dihydro-5H-[2]pyrindin-6-ylmethyl)-8-methyl-2-pyridin-4-yl-6,7,8,9-tetrahydro-pyrimido[1,2-a]pyrimidin-4-one N° 12. 9-(6,7-Dihydro-5H-[1]pyrindin-6-(S)-ylmethyl)-8-methyl-2-pyridin-4-yl-6,7,8,9-tetrahydro-pyrimido[1,2-a]pyrimidin-4-one.

Particularly preferred compounds of the present invention represented by formula (I), wherein R1 is a pyrimidine ring, include also compounds of table 1B:

N° 1. 9-(6,7-Dihydro-5H-cyclopentapyrazin-6-ylmethyl)-7,7-dimethyl-2-pyrimidin-4-yl-6,7,8,9-tetrahydro-pyrimido[1,2-a]pyrimidin-4-one N° 2. (+/−)7,7-Dimethyl-2-(pyrimidin-4-yl)-9-(2-phenyl-6,7-dihydro-5H-[1]pyrindin-6-ylmethyl)-6,7,8,9-tetrahydro-pyrimido[1,2-a]pyrimidine-4-one N° 3. (+/−)9-(2-Chloro-6,7-dihydro-5H-[1]pyrindin-6-ylmethyl)-7,7-dimethyl -2-(pyrimidin-4-yl)-6,7,8,9-tetrahydro-pyrimido[1,2-a]pyrimidin-4-one N° 4. (+/−)-9-(Chroman-3-ylmethyl)-7,7-dimethyl-2-(pyrimidin-4-yl)-6,7,8,9-tetrahydro-pyrimido[1,2-a]pyrimidin-4-one N° 5. (+/−)-9-(6,7-Dihydro-5H-[2]pyrindin-6-ylmethyl)-7,7-dimethyl-2-(pyrimidin-4-yl)-6,7,8,9-tetrahydro-pyrimido[1,2-a]pyrimidin-4-one N° 6. (−)-(S)-9-(2,3-Dihydro-benzofuran-2-ylmethyl)-7,7-dimethyl-2-(pyrimidin-4-yl)-6,7,8,9-tetrahydro-pyrimido[1,2-a]pyrimidin-4-one N° 7. (+/−)-9-(8-Fluoro-5-methoxy-chroman-3-ylmethyl)-7,7-dimethyl-2-(pyrimidin-4-yl)-6,7,8,9-tetrahydro-pyrimido[1,2-a]pyrimidin-4-one N° 8. (+/−)9-(2,3-dihydro-benzo[1,4]dioxin-2-ylmethyl)-7,7-dimethyl-2-(pyrimidin-4-yl)-6,7,8,9-tetrahydro-pyrimido[1,2-a]pyrimidin-4-one N° 9. (+/−)-9-(5-Methoxy-2,3-dihydro-benzo[1,4]dioxin-2-ylmethyl)-7,7-dimethyl-2-(pyrimidin-4-yl)-6,7,8,9-tetrahydro-pyrimido[1,2-a]pyrimidin-4-one N° 10. (−)-(6S)-9-(6,7-Dihydro-5H-[1]pyrindin-6-ylmethyl)-7,7-dimethyl-2-(pyrimidin-4-yl)-6,7,8,9-tetrahydro-pyrimido[1,2-a]pyrimidin-4-one N° 11. (+)-(6R)-9-(6,7-Dihydro-5H-[1]pyrindin-6-ylmethyl)-7,7-dimethyl-2-(pyrimidin-4-yl)-6,7,8,9-tetrahydro-pyrimido[1,2-a]pyrimidin-4-one N° 12. 9-(2-Furo[2,3-b]pyridin-3-yl-ethyl)-7,7-dimethyl-2-(pyrimidin-4-yl)-6,7,8,9-tetrahydro-pyrimido[1,2-a]pyrimidin-4-one N° 13. 9-Benzofuran-2-ylmethyl-7,7-dimethyl-2-pyrimidin-4-yl)-6,7,8,9-tetrahydro-pyrimido[1,2-a]pyrimidin-4-one N° 14. (+/−)-7,7-Dimethyl-9-(2-methyl-6,7-dihydro-5H-[1]pyrindin-6 ylmethyl) -2-(pyrimidin-4-yl)-6,7,8,9-tetrahydro-pyrimido[1,2-a]pyrimidin-4-one.

Particularly preferred compounds of the present invention represented by formula (I), wherein R1 is a pyrimidine, include also compounds of table 2B:

N° 1. 9-(8-Methoxy-2,3-dihydro-benzo[1,4]dioxin-2-ylmethyl)-8-methyl-2-pyrimidin-4-yl-6,7,8,9-tetrahydro-pyrimido[1,2-a]pyrimidin-4-one N° 2. 9-(2,3-Dihydro-benzo[1,4]dioxin-2-ylmethyl)-8,8-dimethyl-2-pyrimidin-4-yl-6,7,8,9-tetrahydro-pyrimido[1,2-a]pyrimidin-4-one N° 3. 9-Chroman-2-ylmethyl-8-methyl-2-pyrimidin-4-yl-6,7,8,9-tetrahydro-pyrimido[1,2-a]pyrimidin-4-one N° 4. 9-(5-Fluoro-8-methoxy-chroman-2-ylmethyl)-8-methyl-2-pyrimidin-4-yl-6,7,8,9-tetrahydro-pyrimido[1,2-a]pyrimidin-4-one N° 5. 9-(5-Fluoro-8-methoxy-chroman-2-ylmethyl)-8,8-dimethyl-2-pyrimidin-4-yl-6,7,8,9-tetrahydro-pyrimido[1,2-a]pyrimidin-4-one N° 6. 9-Chroman-2-ylmethyl-8,8-dimethyl-2-pyrimidin-4-yl-6,7,8,9-tetrahydro-pyrimido[1,2-a]pyrimidin-4-one N° 7. 9-(8-Methoxy-2,3-dihydro-benzo[1,4]dioxin-2-ylmethyl)-8,8-dimethyl-2-pyrimidin-4-yl-6,7,8,9-tetrahydro-pyrimido[1,2-a]pyrimidin-4-one N° 8. 9-(2,3-Dihydro-benzo[1,4]dioxin-2-ylmethyl)-8-methyl-2-pyrimidin-4-yl-6,7,8,9-tetrahydro-pyrimido[1,2-a]pyrimidin-4-one N° 9. 9-(5-Methoxy-2,3-dihydro-benzo[1,4]dioxin-2-ylmethyl)-8-methyl-2-pyrimidin-4-yl-6,7,8,9-tetrahydro-pyrimido[1,2-a]pyrimidin-4-one N° 10. 9-(5-Methoxy-2,3-dihydro-benzo[1,4]dioxin-2-ylmethyl)-8,8-dimethyl-2-pyrimidin-4-yl-6,7,8,9-tetrahydro-pyrimido[1,2-a]pyrimidin-4-one N° 11. 9-(6,7-Dihydro-5H-[1]pyrindin-6-(R)-ylmethyl)-8-methyl-2-pyrimidin-4-yl-6,7,8,9-tetrahydro-pyrimido[1,2-a]pyrimidin-4-one N° 12. 9-(6,7-Dihydro-5H-[1]pyrindin-6-(R)-ylmethyl)-8,8-dimethyl-2-pyrimidin-4-yl-6,7,8,9-tetrahydro-pyrimido[1,2-a]pyrimidin-4-one N° 13. 9-(6,7-Dihydro-5H-[1]pyrindin-6-(S)-ylmethyl)-8,8-dimethyl-2-pyrimidin-4-yl-6,7,8,9-tetrahydro-pyrimido[1,2-a]pyrimidin-4-one N° 14. 9-Furo[3,2-b]pyridin-2-ylmethyl-8-methyl-2-pyrimidin-4-yl-6,7,8,9-tetrahydro-pyrimido[1,2-a]pyrimidin-4-one N° 15. 9-(6,7-Dihydro-5H-[1]pyrindin-6-(S)-ylmethyl)-8-methyl-2-pyrimidin-4-yl-6,7,8,9-tetrahydro-pyrimido[1,2-a]pyrimidin-4-one N° 16. 9-(6,7-Dihydro-5H-[2]pyrindin-6-ylmethyl)-8-methyl-2-pyrimidin-4-yl-6,7,8,9-tetrahydro-pyrimido[1,2-a]pyrimidin-4-one.

As a further object, the present invention concerns also methods for preparing the compounds represented by the aforementioned formula (I).

These compounds can be prepared, for example, according to methods explained below.

Preparation Method

Pyrimidone compounds represented by the aforementioned formula (I) may be prepared according to scheme 1.

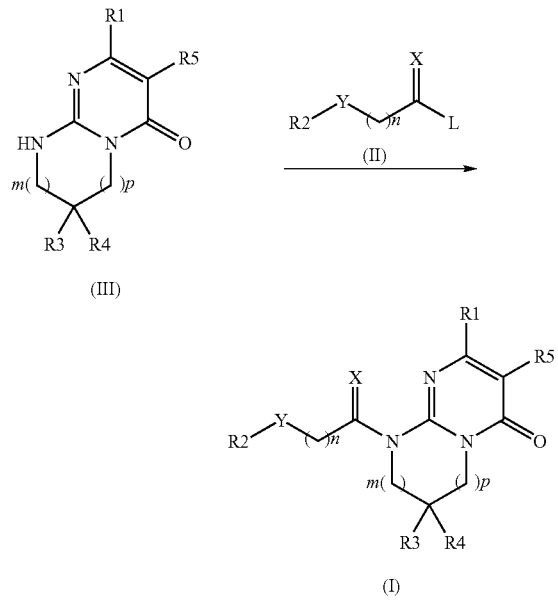

(In the above scheme the definition of R1, R2, R3, R4, R5, X, Y, p, m and n are the same as those already described for compound of formula (I)).

The pyrimidinone derivative represented by the above formula (III), wherein R1 is as defined for compound of formula (I), is allowed to react with a base such as sodium hydride, sodium carbonate or potassium carbonate in a solvent such as N,N-dimethylformamide, N-methylpyrrolidine, N,N-dimethylacetamide or chloroform at a suitable temperature ranging from 0 to 130° C. under ordinary air, then with a compound of formula (II), wherein R2, X, Y and n are as defined for compound of formula (I) and L represents a leaving group preferably bromide or mesyloxy group, is added to obtain the compound of the aforementioned formula (I).

Compound of formula (II) are commercially available or may be synthesised according to well-known methods of one skilled in the art.

For example compounds of formula (II) can be prepared by analogy to the method described in U.S. Pat. No. 5,559,256.

As another example compounds of formula (II) wherein

X represents two hydrogen atoms,

L represents a leaving group, n is 1,

Y represents a bond, and

R2 represents a heterocyclic bicyclic ring of formula:

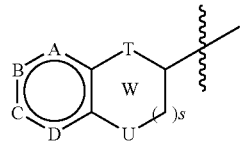

may be prepared by analogy to the method described in U.S. Pat. Nos. 4,957,928 or 5,137,901; or wherein R2 represents a heterocyclic bicyclic ring of formula

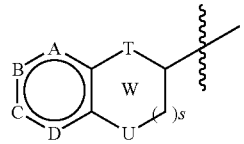

wherein A, B. C and D are defined as above,

T and U represent each a carbon atom and s is 0;

may be prepared by analogy to the method described in WO99/02517 or to scheme 2.

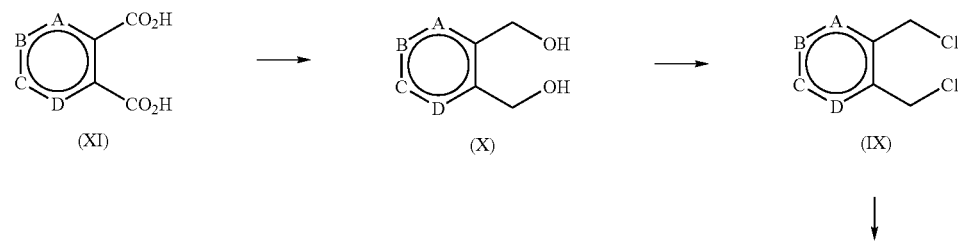

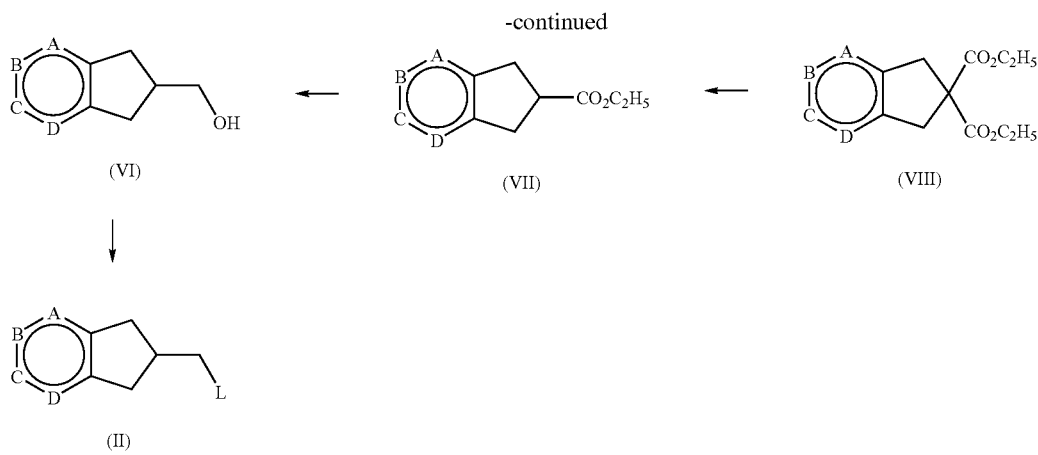

According to the method described in scheme 2, the di-acid of formula (XI), is firstly esterified, for example by action of thionyl chloride in an alcoholic solvent such as ethanol, and then immediately reduced by action of sodium borohydride in the presence of calcium carbonate to give the compound of formula (X). Compound (X) is allowed to react with thionylchloride to give the corresponding bi-chloride compound of formula (IX) which is then transformed into the diester of formula (VIII) by reaction with the sodium dianion derivative of diethylmalonate, in a solvent such as ethanol. Compound (VIII) is then saponified by action of concentrated potassium hydroxide in an alcoholic solvent such as ethanol, neutralised by addition of concentrated chlorhydric acid, decarboxylated by heating and then esterified by treatment with a solution of chlorhydric acid in ethanol, to give compound (VII). The ester (VII) can be separated into its enantiomers using methods well known by one skilled in the art, such as for example, enzymatic way or chemical separation.

The ester of formula (VII) can then be reduced into an alcohol of formula (VI), using for example lithium aluminium hydride in a solvent such as tetrahydrofuran. The hydroxy group is transformed into a leaving group. For example, the alcohol is allowed to react with triphenylphosphine dibromide in a solvent such as dioxan to give compound (II) as defined above, wherein L represent a bromide atom.

The compound of formula (III) may be prepared according to the method defined in scheme 3.

Scheme 3

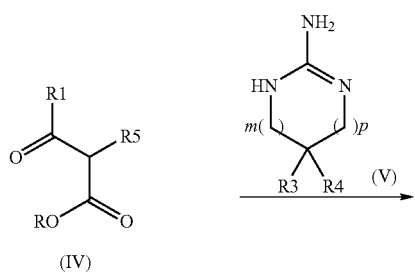

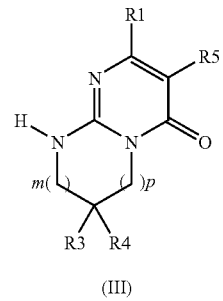

(In the above scheme the definition of R1, R3, R4, R5, p and m are the same as already described.)

According to this method, the 3-ketoester of formula (IV), wherein R1 and R5 are as defined for compound of formula (I) and R is an alkyl group such as for example methyl or ethyl, is allowed to react with a compound of formula (V). The reaction may be carried out in the presence of potassium carbonate, in an alcoholic solvent such as methanol, ethanol and the like or without, at a suitable temperature ranging from 25° to 140° C. under ordinary air.

Alternatively, compounds of formula (III) wherein R5 represents a hydrogen atom may be halogenated in order to give compounds of formula (III) wherein R5 is a halogen atom such as a bromine atom or a chlorine atom. The reaction may be carried out in an acidic medium such as acetic acid or propionic acid, in presence of bromosuccinimide or chlorosuccinimide, or bromine.

In addition, compounds of formula (III) wherein R5 represents a fluorine atom may be obtained by analogy to the method described in Tetrahedron Letters, Vol. 30, N° 45, pp 6113–6116, 1989.

Compounds of formula (V) or (IV) are commercially available or may be synthesised according to well-known methods of one skilled in the art.

For example compounds of formula (IV), wherein R1 represent a pyridine ring or a pyrimidine ring, optionally substituted by a $C_{1-4}$ alkyl group, $C_{1-4}$ alkoxy group or a halogen atom, can be prepared by reacting respectively an isonicotinic acid or a pyrimidine-carboxylic acid, optionally substituted by a $C_{1-4}$ alkyl group, $C_{1-4}$ alkoxy group or a halogen, with the corresponding malonic acid monoester. The reaction can be carried out using methods well known to one skilled in the art, such as for example in presence of a coupling agent such as 1,1'-carbonylbis-1H-imidazole in a solvent such as tetrahydrofuran at a temperature ranging from 20 to 70° C.

Compounds of formula (I) may also be obtained starting from another compound of formula (I) using well-known methods of one skilled in the art.

In the above reactions, protection or deprotection of a functional group may sometimes be necessary. A suitable protecting group Pg can be chosen depending on the type of the functional group, and a method described in the literature may be applied. Examples of protecting groups, of protection and deprotection methods are given for example in Protective groups in Organic Synthesis Greene et al., 2nd Ed. (John Wiley & Sons, Inc., New York).

The compounds of the present invention have inhibitory activity against GSK3β. Accordingly, the compounds of the present invention are useful as an active ingredient for the preparation of a medicament, which enables preventive and/or therapeutic treatment of a disease caused by abnormal GSK3β or GSK3β and cdk5/p25 activity and more particularly of neurodegenerative diseases such as Alzheimer's disease. In addition, the compounds of the present invention are also useful as an active ingredient for the preparation of a medicament for preventive and/or therapeutic treatment of neurodegenerative diseases such as Parkinson's disease, amyotrophic lateral sclerosis, tauopathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies and glaucoma; and other diseases such as non-insulin dependent diabetes (such as diabetes type II) and obesity; manic depressive illness; schizophrenia; alopecia; smoking cessation and other withdrawal syndromes, epilepsy; cancers such as breast cancer, non-small cell lung carcinoma, thyroid cancer, T or B-cell leukemia and several virus-induced tumors.

The present invention further relates to a method for treating neurodegenerative diseases caused by abnormal activity of GSK3β or GSK3β and cdk5/p25 and of the aforementioned diseases which comprises administering to a mammalian organism in need thereof an effective amount of a compound of the formula (I).

As the active ingredient of the medicament of the present invention, a substance may be used which is selected from the group consisting of the compound represented by the aforementioned formula (I) and pharmacologically acceptable salts thereof, and solvates thereof and hydrates thereof. The substance, per se, may be administered as the medicament of the present invention, however, it is desirable to administer the medicament in a form of a pharmaceutical composition which comprises the aforementioned substance as an active ingredient and one or more pharmaceutical additives. As the active ingredient of the medicament of the present invention, two or more of the aforementioned substances may be used in combination. The above pharmaceutical composition may be supplemented with an active ingredient of another medicament for the treatment of the above mentioned diseases. The type of pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like. Injections or drip infusions may be prepared as powdery preparations such as in the form of lyophilised preparations, and may be used by dissolving just before use in an appropriate aqueous medium such as physiological saline. Sustained-release preparations such as those coated with a polymer may be directly administered intracerebrally.

Types of pharmaceutical additives used for the manufacture of the pharmaceutical composition, content ratios of the pharmaceutical additives relative to the active ingredient, and methods for preparing the pharmaceutical composition may be appropriately chosen by those skilled in the art. Inorganic or organic substances, or solid or liquid substances may be used as pharmaceutical additives. Generally, the pharmaceutical additives may be incorporated in a ratio ranging from 1% by weight to 90% by weight based on the weight of an active ingredient.

Examples of excipients used for the preparation of solid pharmaceutical compositions include, for example, lactose, sucrose, starch, talc, cellulose, dextrin, kaolin, calcium carbonate and the like. For the preparation of liquid compositions for oral administration, a conventional inert diluent such as water or a vegetable oil may be used. The liquid composition may contain, in addition to the inert diluent, auxiliaries such as moistening agents, suspension aids, sweeteners, aromatics, colorants, and preservatives. The liquid composition may be filled in capsules made of an absorbable material such as gelatine. Examples of solvents or suspension mediums used for the preparation of compositions for parenteral administration, e.g. injections, suppositories, include water, propylene glycol, polyethylene glycol, benzyl alcohol, ethyl oleate, lecithin and the like. Examples of base materials used for suppositories include, for example, cacao butter, emulsified cacao butter, lauric lipid, witepsol.

The dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 100 mg (the weight of an active ingredient) to an adult.

CHEMICAL EXAMPLES

The present invention will be explained more specifically with reference to the following general examples, however, the scope of the present invention is not limited to these examples.

Part A—R1=Pyridine Ring (Tables 1A and 2A)

Example 1

Compound N° 1 of Table 1A (+)-(6R)-9-(6,7-Dihydro-5H-[1]pyrindin-6-ylmethyl)-7,7-dimethyl-2-(pyridin-4-yl)-6,7,8,9-tetrahydro-pyrimido[1,2-a]pyrimidin-4-one 1.1 7,7-Dimethyl-2-(pyridin-4-yl)-6,7,8,9-tetrahydro-4H-pyrimido[1,2-a]pyrimidin-4-one A mixture of 5.9 g (30.55 mmol) of ethyl 3-(4-pyridyl)-3-oxopropionate, 5.0 g (30.55 mmol) of 5,5-dimethyl-1,4, 5,6-tetrahydro-2-pyrimidinamine monohydrochloride (prepared by analogy to U.S. Pat. No. 4,262,122) and 6.33 g (45.82 mmol) of potassium carbonate in 60 ml of ethanol was heated at reflux temperature during 12 h. The cooled suspension was filtered and the solvent removed by evaporation. The residue obtained was dissolved in dichloromethane and washed with water. The organic phase was dried and evaporated to give 6.30 g (80%) of product as a beige solid. Mp.: 152–154° C.

1.2 (−)-(6R,5R)-(6,7-Dihydro-5H-[1]pyrindin-6-yl)-(10,10-dimethyl-3,3-dioxa-3-thia-4-aza-tricyclo[5.2.1.0<1,5>]decyl-4-yl]-methanone A suspension of 12 g (73.56 mmol) of (+/−)-6,7-dihydro-5H-[1]pyrindine-6-carboxylic acid (prepared by analogy with WO 99/02517) in 85 ml of anhydrous dimethylformamide was treated with 13.36 g (82.39 mmol) of 1,1'-carbonyldiimidazole and the resulting mixture was heated at 45° C. for 1 h. 15.84 g (73.56 mmol) of (−)-10,2-camphorsultam (Fluka) and 11.2 g (73.56 mmol) of 1,8-diazabicyclo[5,4,0]undec-7-ene were added and the reaction mixture was stirred at 40° C. for 18 h.

The precipitate solid was recovered by filtration, washed with ethyl acetate, diethyl ether and dried, affording 20.8 g (79%) of product as a white solid.

Mp.: 270–272° C. $[\alpha]_D^{20}$=−151° (c=1, CHCl$_3$).

1.3 (+)-(6R)-6,7-Dihydro-5H-[1]pyrindine-6-carboxylic acid

To a solution of 20.6 g (57.15 mmol) of (−)-(6R,5R)-(6,7-Dihydro-5H-[1]pyrindin-6-yl)-(10,10-dimethyl-3,3-dioxa-3-thia-4-aza-tricyclo[5.2.1.0<1,5>]dec-4-yl]-methanone in 300 ml of tetrahydrofuran/water in the proportions 2:1 was added 2.88 g (68.6 mmol) of lithium hydroxide. The mixture was allowed to stir at room temperature for 5 h. Water was added, and the reaction mixture was extracted with ethyl acetate. The aqueous phase was acidified to pH 6 with acetic acid. The precipitate obtained was filtered off and dried to give 7.5 g (81%) of white solid. Mp.: 236–237 $[\alpha]_D^{20}$=+5.4° (c=0.5, dimethylformamide).

1.4 (+)-(6R)-(6,7-Dihydro-5H-[1]pyrindin-6-yl)-methanol

To a solution of 3.26 g (20 mmol) of (+)-6,7-dihydro-5H-[1]pyrindine-6-carboxylic acid in 100 ml of anhydrous tetrahydrofuran under argon was added 1.14 g (30 mmol) of lithium aluminium hydride. The resulting mixture was stirred at room temperature for 1 h. Excess of lithium aluminium hydride was hydrolysed with 4.56 ml of water and 1.14 ml of sodium hydroxide (15%). The precipitate was filtered off and washed with diethyl ether, the filtrate was evaporated to give 2.88 g (97%) of product as an oil. $[\alpha]_D^{20}$=+6.2° (c=0.75, CH$_2$Cl$_2$).

1.5 Methanesulfonic acid 6,7-dihydro-5H-[1]pyrindin-6-ylmethyl ester

To a solution of 895 mg (6 mmol) of (+)-(6R)-(6,7-dihydro-5H-[1]pyrindin-6-yl)-methanol in 50 ml of anhydrous dichloromethane was added at −15° C. 0.918 ml (6.6 mmol) of triethylamine and 0.465 ml (6 mmol) of methanesulfonyl chloride. The resulting mixture was stirred at 0° C. for 45 min. The mixture was then diluted with water and dichloromethane and extracted with dichloromethane. Organic layer was dried and evaporated to give 1.4 g (100%) of methanesulfonic acid 6,7-dihydro-5H-[1]pyrindin-4-ylmethyl ester.

1.6 (+)-(6R)-9-(6,7-Dihydro-5H-[1]pyrindin-6-ylmethyl)-7,7-dimethyl-2-(pyridin-4-yl)-6,7,8,9-tetrahydro-pyrimido[1,2-a]pyrimidin-4-one A suspension of 0.51 g (2 mmol) of 7,7-dimethyl-2-(pyridin-4-yl)-6,7,8,9-tetrahydro-4H-pyrimido[1,2-a]pyrimidin-4-one in 10 ml of anhydrous dimethylformamide was treated with 96 mg (2 mmol) of sodium hydride (50% suspension in mineral oil) and the resulting mixture was stirred for 40 min. 0.455 g (2 mmol) of methanesulfonic acid 6,7-dihydro-5H-[1]pyrindin-6-ylmethyl ester in 2 ml of anhydrous dimethylformamide was added and the reaction mixture stirred at room temperature for 18 h.

The solution was treated with water and extracted with ethyl acetate. The organic phase was dried and evaporated to give crude product, which was purified by silica gel chromatography, eluting with ethyl acetate/methanol/diethyl amine in the proportions 98/2/0.2 to give 0.383 g of pure product obtained in the form of free base. Mp: 182–184° C. $[\alpha]_D^{20}$=+9.15° (c=0.5, CH$_2$Cl$_2$).

Example 2

Compound N° 2 of Table 1A (−)-(6S)-9-(6,7-Dihydro-5H-[1]pyrindin-6 ylmethyl)-7,7-dimethyl-2-(pyridin-4-yl)-6,7,8,9-tetrahydro-pyrimido[1,2-a]pyrimidin-4-one 2.1 By analogy with the method described in example 1, using (+)-10,2-camphorsultam (Fluka) in place of (−)-10,2-camphorsultam in step 1.2, the compound was obtained as a free base. Mp.: 182–185° C. $[\alpha]_D^{20}$=−6.6° (c=0.5, CH$_2$Cl$_2$).

Example 3

Compound N° 3 of Table 1A (+)-(6R)-9-(6,7-Dihydro-5H-[1]pyrindin-6 ylmethyl)-2-(pyridin-4-yl)-6,7,8,9-tetrahydro-pyrimido[1,2-a]pyrimidin-4-one

3.1. 2-(Pyridin-4-yl)-6,7,8,9-tetrahydro-4H-pyrimido[1,2-a]pyrimidin-4-one

A mixture of 8.98 g (46.5 mmol) of ethyl 3-(4-pyridyl)-3-oxopropionate and 8.0 g (46.5 mmol) of 2-amino-3,4,5,6-tetrahydropyrimidine dihydrochloride (prepared according to J. Org. Chem. 1955, 20, 829) and 19.3 g (139.5 mmol) of potassium carbonate in 60 ml of ethanol was heated at reflux temperature during 18 h.

The solution cooled, was evaporated to remove solvent. The residue was treated with water and extracted with dichloromethane. The extracts were dried and evaporated to give 8.0 g (75%) of product as a white powder. Mp: 219° C.

3.2 (+)-(6R)-9-(6,7-Dihydro-5H-[1]pyrindin-6-ylmethyl)-2-(pyridin-4-yl)-6,7,8,9-tetrahydro-pyrimido[1,2-a]pyrimidin-4-one A suspension of 0.46 g (2 mmol) of 2-(pyridin-4-yl)-6,7,8,9-tetrahydro-4H-pyrimido[1,2-a]pyrimidin-4-one in 10 ml of anhydrous dimethylformamide was treated with 96 mg (2 mmol) of sodium hydride (50% suspension in mineral oil) and the resulting mixture was stirred for 40 min. 0.455 g (2 mmol) of methanesulfonic acid 6,7-dihydro-5H-[1]pyrindin-6-ylmethyl ester in 2 ml of anhydrous dimethylformamide was added and the reaction mixture stirred at 45° C. for 18 h.

The solution was treated with water and extracted with ethyl acetate. The organic phase was dried and evaporated to give crude product, which was purified by silica gel chromatography, eluting with ethyl acetate/methanol/ammonia in the proportions 90/10/1 to give 0.373 g of pure product obtained in the form of free base. Mp: 174–175° C.

[α]$_D^{20}$=+10.5° (c=1, CH$_2$Cl$_2$).

Example 4

Compound N° 4 of Table 1A (+/−)-7,7-Dimethyl-9-(2-methyl-6,7-dihydro-5H-[1]-pyrindin-6-ylmethyl)-2-(pyridin-4-yl)-6,7,8,9-tetrahydro-pyrimido[1,2-a]pyrimidin-4-one By analogy with the method described in example 1, using (+/−)2-methyl-6,7-dihydro-5H-[1]pyrindine-6-carboxylic acid instead of (+/−)-6,7-dihydro-5H-[1]pyrindine-6-carboxylic acid, the compound was obtained as a free base.

Mp.: 140–141° C.

Example 5

Compound N° 5 of Table 1A (+)-7,7-Dimethyl-9-(2-methyl-6,7-dihydro-5H-[1]-pyrindin-6-ylmethyl)-2-(pyridin-4-yl)-6,7,8,9-tetrahydro-pyrimido[1,2-a]pyrimidin-4-one 180 mg (0.45 mmol) of (+/−)-7,7-Dimethyl-9-(2-methyl-6,7-dihydro-5H-[1]-pyrindin-6-ylmethyl)-2-(pyridin-4-yl)-6,7,8,9-tetrahydro-pyrimido[1,2-a]pyrimidin-4-one (compound N° 4) was separated by chiral preparative HPLC (CHIRALCEL OD 250×20) eluting with heptane/ethanol/diethylamine in the proportions 85/15/0.1 to give 0.071 g of pure product obtained in the form of free base. t$_R$: 12.48 min. Mp: 94–96° C. [α]$_D^{20}$=+6.79° (c=0.5, CH$_2$Cl$_2$).

Example 6

Compound N° 6 of Table 1A (−)-7,7-Dimethyl-9-(2-methyl-6,7-dihydro-5H-[1]-pyrindin-6-ylmethyl)-2-(pyridin-4-yl)-6,7,8,9-tetrahydro-pyrimido[1,2-a]pyrimidin-4-one 180 mg (0.45 mmol) of (+/−)-7,7-Dimethyl-9-(2-methyl-6,7-dihydro-5H-[1]-pyrindin-6-ylmethyl)-2-(pyridin-4-yl)-6,7,8,9-tetrahydropyrimido[1,2-a]pyrimidin-4-one (compound N° 4) was separated by chiral preparative HPLC (CHIRALCEL OD 250×20) eluting with heptane/ethanol/diethylamine in the proportions 85/15/0.1 to give 0.075 g of pure product obtained in the form of free base. t$_R$: 17.25 min. Mp: 94–96 C. [α]$_D^{20}$=−5.61° (c=0.5, CH$_2$Cl$_2$).

Example 7

Compound N° 7 of Table 1A (+/−)-9-(2,3-Dihydro-benzofuran-2-ylmethyl)-7,7-dimethyl-2-(pyridin-4-yl)-6,7,8,9-tetrahydro-pyrimido[1,2-a]pyrimidin-4-one A suspension of 0.51 g (2 mmol) of 7,7-dimethyl-2-(pyridin-4-yl)-6,7,8,9-tetrahydro-4H-pyrimido[1,2-a]pyrimidin-4-one in 10 ml of anhydrous dimethylformamide was treated with 96 mg (2 mmol) of sodium hydride (50% suspension in mineral oil) and the resulting mixture was stirred at 40° C. for 40 min. 0.52 g (2 mmol) of (+/−)2-iodomethyl-2,3-dihydro-benzofuran (prepared according to Synthesis 1997, (1), 23–25) in 2 ml of anhydrous dimethylformamide was added and the reaction mixture stirred at 60° C. for 20 min.

The solution was treated with water and extracted with ethyl acetate. The organic phase was dried and evaporated to give crude product, which was purified by silica gel chromatography, eluting with dichloromethane/methanol/ammonia in the proportions 99/1/0.1 to 98/2/0.2 to give 0.171 g of pure product obtained in the form of free base. Mp: 147–149° C.

Example 8

Compound N° 8 of Table 1A 9-(Furo[3,2-b]pyridin-2-ylmethyl)-7,7-dimethyl-2-(pyridin-4-yl)-6,7,8,9-tetrahydro-pyrimido[1,2-a]pyrimidin-4-one 8.1 Methanesulfonic acid furo[3,2-b]pyridin-2-ylmethyl ester The product was obtained by analogy with the method described in step 1.5 and using furo[3,2-b]pyridin-2-ylmethanol (U.S. Pat. No. 5,559,256 or EP 580402) and was used as such in the next step.

8.2 9-Furo[3,2-b]pyridin-2-ylmethyl-7,7-dimethyl-2-(pyridin-4-yl)-6,7,8,9-tetrahydro-pyrimido[1,2-a]pyrimidin-4-one By analogy with the method described in step N° 1.6, using methanesulfonic acid furo[3,2-b]pyridin-2-ylmethyl ester, the compound was obtained in the form of free base. Mp: 170–171° C.

Example 9

Compound N° 10 of Table 1A (+/−)-9-(2-Chloro-6,7-dihydro-5H-[1]pyrindin-6-ylmethyl)-7,7-dimethyl-2-(pyridin-4-yl)-6,7,8,9-tetrahydro-pyrimido[1,2-a]pyrimidin-4-one 9.1 (+/−)(2-Chloro-6,7-dihydro-5H-[1]pyrindin-6-yl)-methanol To a solution of 1.83 g (9.26 mmol) of (+/−)2-chloro-6,7-dihydro-5H-[1]pyrindine-6-carboxylic acid (prepared by analogy to the method described in WO 99/02517) in 50 ml of anhydrous tetrahydrofuran under argon was added 0.52 g (13.89 mmol) of lithium aluminium hydride. The resulting mixture was stirred at room temperature for 2 h. Excess of lithium aluminium hydride was hydrolysed with 2.13 ml of water and 0.53 ml of sodium hydroxide (15%). The precipitate was filtered off and washed with diethyl ether, the filtrate was evaporated to give 1.61 g (95%) of product as an oil.

9.2 (+/−)Methanesulfonic acid 2-chloro-6,7-dihydro-5H-[1]pyrindin-6-yl-methyl ester The product was obtained by analogy with the method described in step 1.5 and using (+/−)(2-chloro-6,7-dihydro-5H-[1]pyrindin-6-yl)-methanol. The product was used as such in the next step.

9.3 (+/−)9-(2-Chloro-6,7-dihydro-5H-[1]pyrindin-6-ylmethyl)-7,7-dimethyl-2-(pyridin-4-yl)-6,7,8,9-tetrahydro-pyrimido[1,2-a]pyrimidin-4-one The product was obtained by analogy with the method described in step N° 1.6, using (+/−)Methanesulfonic acid 2-chloro-6,7-dihydro-5H-[1]pyrindin-6-yl-methyl ester. The compound was obtained in the form of free base. Mp: 180–181° C.

Example 10

Compound N° 11 of Table 1A (+/−)7,7-Dimethyl-2-(pyridin-4-yl)-9-[2-(pyridin-4-yl)-6,7-dihydro-5H-[1]pyrindin-6-ylmethyl]-6,7,8,9-tetrahydro-pyrimido[1,2-a]pyrimidine-4-one To a solution of 0.22 g (0.521 mmol) of (+/−)9-(2-chloro-6,7-dihydro-5H-[1]pyrindin-6-ylmethyl)-7,7-dimethyl-2-(pyridin-4-yl)-6,7,8,9-tetrahydro-pyrimido[1,2-a]pyrimidin-4-one in 3 ml of anhydrous toluene and 0.5 ml of ethanol was treated with 0.625 ml (2M solution in water) of sodium carbonate, 36 mg (0.03 mmol) of tetrakis(triphenylphosphine)palladium and 0.096 g (0.781 mmol) of pyridine-4-boronic acid. After being stirred for 24 h at 140° C., water was added, the mixture was extracted with dichloromethane. The organic phase was dried and evaporated to give crude product, which was purified by silica gel chromatography, eluting with dichloromethane/methanol/ammonia in the proportions 99/1/0.1 to give 0.049 g of pure product obtained in the form of free base. Mp: 170–171° C.

Example 11

Compound N° 13 of Table 1A (+/−)7,7-Dimethyl-2-(pyridin-4-yl)-9-[(2-pyrrolidin-1-yl-6,7-dihydro-5H-[1]pyrindin-6-ylmethyl)]-6,7,8,9-tetrahydro-pyrimido[1,2-a]pyrimidin-4-one To a solution of 0.2 g (0.474 mmol) of (+/−)9-(2-chloro-6,7-dihydro-5H-[1]pyrindin-6-ylmethyl)-7,7-dimethyl-2-(pyridin-4-yl)-6,7,8,9-tetrahydro-pyrimido[1,2-a]pyrimidin-4-one in 20 ml of anhydrous pyrrolidine was treated with 0.216 g (0.664 mmol) of cesium carbonate, 8.85 mg (0.142 mmol) of (S)-(−)-2,2'-bis(diphenylphosphino)-1,1'-binaphthyl and 6.5 mg (0.07 mmol) of tris(dibenzylideneacetone) dipalladium(0). After being stirred under reflux for 24 h, water was added, the mixture was extracted with dichloromethane. The organic phase was dried and evaporated to give crude product, which was purified by silica gel chromatography, eluting with dichloromethane/methanol/ammonia in the proportions 99/1/0.1 to give 0.184 g of pure product obtained in the form of free base. Mp: 170–171° C.

Example 12

Compound N° 14 of Table 1A (+/−)7,7-Difluoro-9-(2-methyl-6,7-dihydro-5H-[1]pyrindin-6-ylmethyl)-2-(pyridin-4-yl)-6,7,8,9-tetrahydro-pyrimido[1,2-a]pyrimidine-4-one hydrochloride (1:2)

12.1
5,5-Difluoro-1,4,5,6-tetrahydro-2-pyrimidinamine

The product was obtained by analogy with the method described in U.S. Pat. No. 4,262,122 and using 2,2-difluoro-1,3-propandiamine (Tetrahedron (1994) 50(29), 8617–8632) and was used as such in the next step.

12.2 7,7-Difluoro-2-pyridinyl)-6,7,8,9-tetrahydro-pyrimido[1,2-a]pyrimidin-4-one The product was obtained by analogy with step N° 3.1 and using 5,5-difluoro-1,4,5,6-tetrahydro-2-pyrimidinamine from step 12.1. Mp: 239–240° C.

12.3 (+/−)7,7-Difluoro-9-(2-methyl-6,7-dihydro-5H-[1]pyrindin-6-ylmethyl)-2-(pyridin-4-yl)-6,7,8,9-tetrahydro-pyrimido[1,2-a]pyrimidine-4-one hydrochloride (1:2)

The product was obtained by analogy with the method described in step N° 1.6 the compound was obtained in the form of free base which was transformed into the hydrochloride salt. Mp: 236–238° C.

Example 13

Compound N° 15 of Table 1A 9-((+)-(6-R)-6,7-Dihydro-5H-[1]pyrindin-6-ylmethyl)-7-methyl-2-(pyridin-4-yl)-6,7,8,9-tetrahydro-pyrimido[1,2-a]pyrimidine-4-one 13.1 5-Methyl-1,4,5,6-tetrahydro-2-pyrimidinamine hydrochloride To a solution containing 6.7 g (41.6 mmol) of 2-methyl-1,3-propanediamine hydrochloride (Tetrahedron (1994) 50(29), 8617–8632) in 50 ml of methanol was added 83 ml of a solution of sodium methylate in methanol (1 mmol/ml) and the resulting mixture was treated with 3.97 g (41.6 mmol) of guanidine hydrochloride. The reaction mixture was heated at 140° C. for 3 h. The solution was filtered, the solvent evaporated and the residue obtained was used directly in the next step.

13.2 (+/−)-7-Methyl-2-(pyridin-4-yl)-6,7,8,9-tetrahydro-4H-pyrimido[1,2a]pyrimidin-4-one The product was obtained by analogy with step N° 3.1 and using the intermediate from step N° 13.1.

13.3 9-((+)-(6-R)-6,7-Dihydro-5H-[1]pyrindin-6-ylmethyl)-7-methyl-2-pyridin-4-yl-6,7,8,9-tetrahydro-pyrimido[1,2-a]pyrimidine-4-one The product was obtained by analogy with the method described in step N° 1.6, using (+/−)-7-methyl-2-(pyridin-4-yl)-6,7,8,9-tetrahydro-4H-pyrimido[1,2-a]pyrimidin-4-one. The compound was obtained in the form of free base. Mp: 156–157° C.

Example 14

Compound No. 10 of Table 2A 9-(6,7-Dihydro-5H-[1]pyrindin-6-(R)-ylmethyl)-8-methyl-2-pyridin-4-yl-6,7,8,9-tetrahydro-pyrimido[1,2-a]pyrimidin-4-one 14.1 8-Methyl-2-(pyridin-4-yl)-6,7,8,9-tetrahydro-pyrimido[1,2-a]pyrimidin-4-one A mixture of 6 g (31.0 mmol) of ethyl 3-(pyridinyl)-3-oxopropionate, 4.6 g (31.0 mmol) of 6-methyl-1,4,5,6-tetrahydro-pyrimidin-2-ylamine hydrochloride (prepared according to J. Org. Chem., 20, 1955, 829–838) and 6.44 g (46.0 mmol) of potassium carbonate in 50 ml of ethanol was heated at reflux temperature during 18 h. The reaction mixture was cooled and the solvent removed by evaporation.

The residue obtained was treated with water and the precipitate recovered by filtration to give 3.85 g (51%) of product.

Mp.: 245–247° C.

14.2 9-(6,7-Dihydro-5H-[1]pyrindin-6-(R)-ylmethyl)-8-methyl-2-pyridin-4-yl-6,7,8,9-tetrahydro-pyrimido[1,2-a]pyrimidin-4-one To a solution of 0.15 g (0.62 mmol) of 8-methyl-2-(pyridin-4-yl)-6,7,8,9-tetrahydro-pyrimido[1,2-a]pyrimidin-4-one in 3 ml of anhydrous dimethylformamide was added 0.032 g (0.81 mmol) of sodium hydride (60% suspension in mineral oil). The mixture was allowed to stir at 50° C. for 30 min. 0.184 g (0.81 mmol) of methanesulfonic acid 6,7-dihydro-5H-[1]pyrindin-6-(R)-ylmethyl ester was added and the stirring continued at 85° C. for 18 h. Water was added and the mixture extracted with trichloromethane/methanol 90/10. The extracts were washed with a saturated aqueous solution of sodium chloride, dried and evaporated to give crude product. Purification by chromatography on silica gel, eluting with a mixture of ethylacetate/ethanol in the proportions 100/0 to 74/26, gives 0.14 g (60%) of the compound in the form of free base.

Mp.: 164–166° C.

Example 15

Compound No. 5 in Table 2A 9-(6,7-Dihydro-5H-[1]pyrindin-6-(R)-ylmethyl)-8,8-dimethyl-2-pyridin-4-yl-6,7,8,9-tetrahydro-pyrimido[1,2-a]pyrimidin-4-one

15.1 8,8-Dimethyl-2-(pyridin-4-yl)-6,7,8,9-tetrahydro-pyrimido[1,2-a]pyrimidin-4-one A mixture of 7.68 g (39.8 mmol) of ethyl 3-(pyridin-4-yl)-3-oxopropionate, 7.9 g (37.9 mmol) of 6,6-dimethyl-1,4,5,6-tetrahydro-pyrimidin-2-ylamine hydrobromide (prepared according to Bull. Soc. Chim. Belg., 1950, 59, 573–587) and 11 g (79.5 mmol) of potassium carbonate in 80 ml of ethanol were heated at reflux temperature during 18 h.

The reaction mixture was cooled and the solvent removed by evaporation. The residue obtained was treated with water and the precipitate recovered by filtration to give 3.21 g (33%) of product.

15.2 9-(6,7-Dihydro-5H-[1]pyrindin-6-(R)-ylmethyl)-8,8-dimethyl-2-pyridin-4-yl-6,7,8,9-tetrahydro-pyrimido[1,2-a]pyrimidin-4-one To a solution of 0.226 g (0.88 mmol) of 8,8-dimethyl-2-(pyridin-4-yl)-6,7,8,9-tetrahydro-pyrimido[1,2-a]pyrimidin-4-one in 5 ml of anhydrous dimethylformamide was added 0.040 g (0.97 mmol) of sodium hydride (60% suspension in mineral oil) and the mixture was allowed to stir at 45° C. for 3 hours. 0.20 g (0.88 mmol) of methanesulfonic acid 6,7-dihydro-5H-[1]pyrindin-6-(R)-ylmethyl ester was added and the stirring continued at 80° C. for 18 h. The mixture was cooled and a solution of saturated ammonium chloride was added. The mixture was extracted with trichloromethane/methanol 90/10. The extracts were washed with a saturated aqueous solution of sodium chloride, dried and evaporated to give crude product. Purification by chromatography on silica gel eluting with a mixture of ethylacetate/ethanol in the proportions 100/0 to 70/20, gives 0.197 g (58%) of the compound in the form of free base.

Mp.: 202–204° C.

A list of chemical structures and physical data for compounds of the aforementioned formula (I), wherein R1 is a pyridine ring, illustrating the present invention is given in table 1A and 2A. The compounds have been prepared according to the methods of the examples.

In the tables:
(rac.) means racemic mixture
(−) means levo isomer
(+) means dextro isomer
(R) means absolute R configuration
(S) means absolute S configuration In the tables 1A and 2A, R1 is an unsubstituted 4-pyridine ring (4-py); in the column "X", when X represents two hydrogen atoms, only "H" is indicated and for compounds of formula (I) "m" and "p" equal 1.

TABLE 1A (I)

| N° | X | Y | R2 | R3 | R4 | R5 | n | Mp ° C. | salt |
|---|---|---|---|---|---|---|---|---|---|
| 1 | H | bond | 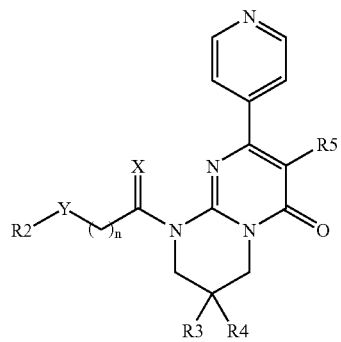 (+) - (R) | CH₃ | CH₃ | H | 0 | 182–184 | Free base |

TABLE 1A-continued (I)

| N° | X | Y | R2 | R3 | R4 | R5 | n | Mp ° C. | salt |
|---|---|---|---|---|---|---|---|---|---|
| 2 | H | bond | 2,3-dihydro-1H-cyclopenta[b]pyridin-6-yl-methyl (−)-(S) | CH₃ | CH₃ | H | 0 | 182–185 | Free base |
| 3 | H | bond | 2,3-dihydro-1H-cyclopenta[b]pyridin-6-yl-methyl (+)-(R) | H | H | H | 0 | 174–175 | Free base |
| 4 | H | bond | 2-methyl-6,7-dihydro-5H-cyclopenta[b]pyridin-6-yl (Rac.) | CH₃ | CH₃ | H | 0 | 140–141 | Free base |
| 5 | H | bond | 2-methyl-6,7-dihydro-5H-cyclopenta[b]pyridin-6-yl (+) | CH₃ | CH₃ | H | 0 | 94–96 | Free base |
| 6 | H | bond | 2-methyl-6,7-dihydro-5H-cyclopenta[b]pyridin-6-yl (−) | CH₃ | CH₃ | H | 0 | 94–96 | Free base |
| 7 | H | bond | 2,3-dihydrobenzofuran-2-yl (Rac.) | CH₃ | CH₃ | H | 0 | 147–149 | Free base |
| 8 | H | bond | furo[3,2-b]pyridin-2-yl | CH₃ | CH₃ | H | 0 | 170–171 | Free base |
| 9 | H | bond | benzofuran-2-yl | CH₃ | CH₃ | H | 0 | 176–177 | Free base |
| 10 | H | bond | 2-chloro-6,7-dihydro-5H-cyclopenta[b]pyridin-6-yl (Rac.) | CH₃ | CH₃ | H | 0 | 180–181 | Free base |

TABLE 1A-continued
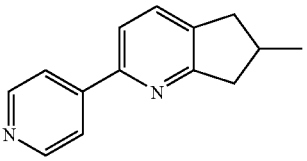
(I)
| N° | X | Y | R2 | R3 | R4 | R5 | n | Mp ° C. | salt |
|----|---|---|----|----|----|----|----|---------|------|
| 11 | H | bond | 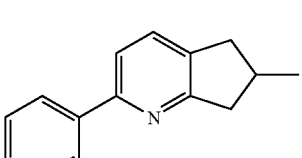 (Rac.) | CH₃ | CH₃ | H | 0 | 170–171 | Free base |
| 12 | H | bond |  (Rac.) | CH₃ | CH₃ | H | 0 | 165–168 | Free base |
| 13 | H | bond | 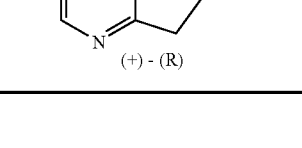 (Rac.) | CH₃ | CH₃ | H | 0 | 170–171 | Free base |
| 14 | H | bond | 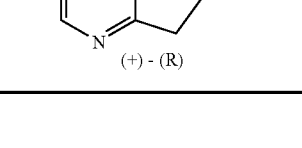 (Rac.) | F | F | H | 0 | 236–238 | (1:2)hydrochloride |
| 15 | H | bond | 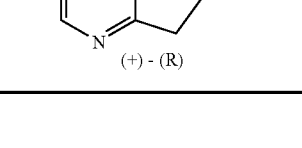 (+) - (R) | H | CH₃(Rac.) | H | 0 | 156–157 | Free base |

TABLE 2A
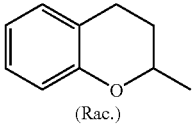
(I)
| N° | X | Y | R2 | R3 | R4 | R5 | n | Mp ° C. | salt |
|---|---|---|---|---|---|---|---|---|---|
| 1 | H | bond | 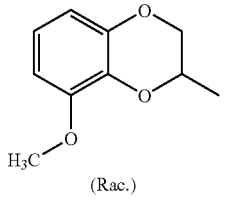 (Rac.) | H | CH$_3$(Rac.) | H | 0 | 178–180 | Free base |
| 2 | H | bond | 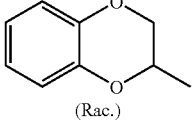 (Rac.) | H | CH$_3$(Rac.) | H | 0 | 258–260 | (1:1)hydrochloride |
| 3 | H | bond | 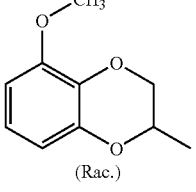 (Rac.) | H | CH$_3$(Rac.) | H | 0 | 164–166 | Free base |
| 4 | H | bond | 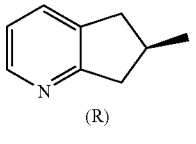 (Rac.) | H | CH$_3$(Rac.) | H | 0 | 146–148 | Free base |
| 5 | H | bond | 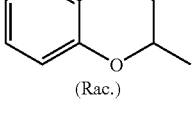 (R) | CH$_3$ | CH$_3$ | H | 0 | 202–204 | Free base |
| 6 | H | bond | 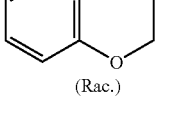 (Rac.) | CH$_3$ | CH$_3$ | H | 0 | 169–171 | (1:1)hydrochloride |
| 7 | H | bond |  (Rac.) | CH$_3$ | CH$_3$ | H | 0 | 151–153 | Free base |

TABLE 2A-continued (I)

| N° | X | Y | R2 | R3 | R4 | R5 | n | Mp ° C. | salt |
|---|---|---|---|---|---|---|---|---|---|
| 8 | H | bond | 3-methyl-8-fluoro-5-methoxychroman (Rac.) | CH₃ | CH₃ | H | 0 | 211–213 | Free base |
| 9 | H | bond | 2-methylfuro[3,2-b]pyridine | H | CH₃(Rac.) | H | 0 | 137–139 | (2:1)hydrochloride |
| 10 | H | bond | (R)-6-methyl-6,7-dihydro-5H-cyclopenta[b]pyridine | H | CH₃(Rac.) | H | 0 | 164–166 | Free base |
| 11 | H | bond | 6-methyl-6,7-dihydro-5H-cyclopenta[c]pyridine (Rac.) | H | CH₃(Rac.) | H | 0 | 146–148 | Free base |
| 12 | H | bond | (S)-6-methyl-6,7-dihydro-5H-cyclopenta[b]pyridine | H | CH₃(Rac.) | H | 0 | 173–175 | Free base |

Part B—R1=Pyrimidine Ring (Tables 1B and 2B)

Example 1

Compound N° 1 of Table 1B 9-(6,7-Dihydro-5H-cyclopentapyrazin-6-ylmethyl)-7,7-dimethyl-2-(pyrimidin-4-yl)-6,7,8,9 tetrahydropyrimido[1,2-a]pyrimidin-4-one 1.1 7,7-Dimethyl-2-(pyrimidin-4-yl)-6,7,8,9-tetrahydro-4H-pyrimido[1,2-a]pyrimidin-4-one A mixture containing 5.15 g (26.52 mmol) of ethyl 3-(4-pyrimidinyl)-3-oxopropionate, (prepared by analogy to the method described in patent DE 2705582), 4.34 g (26.52 mmol) of 5,5-dimethyl-1,4,5,6-tetrahydro-2-pyrimidinamine monohydrochloride (prepared by analogy to the method described in U.S. Pat. No. 4,262,122) and 3.66 g (26.5 mmol) of potassium carbonate in 60 ml of methanol were heated at reflux temperature during 18 h. The cooled reaction mixture was evaporated and water was added. The resulting precipitate was recovered by filtration and dried to give 4.86 g (71%) of product. Mp.: 194–196° C.

1.2 (6,7-Dihydro-5H-cyclopentapyrazin-6-yl)-methanol

To a solution of 4.5 g (23.4 mmol) of 6,7-dihydro-5H-cyclopentapyrazine-6 carboxylic acid ethyl ester (prepared by analogy to the method described in WO99/02517) in 90 ml of anhydrous tetrahydrofuran under argon was added 1.33 g (35.1 mmol) of lithium aluminium hydride. The resulting mixture was stirred at room temperature for 2 h. The reaction mixture was diluted with 100 ml of diethylether at 0° C. and treated with excess of a saturated aqueous solution of sodium sulfate. Further solid sodium sulfate was added and the organic phase was filtered to remove salts. The solvent was evaporated to dryness to give 3.3 g (94%) of product as an oil.

1.3 Methanesulfonic acid 6,7-dihydro-5H-cyclopentapyrazin-6-ylmethyl ester

To a solution of 1.3 g (8.7 mmol) of (6,7-dihydro-5H-cyclopentapyrazin-6-yl)-methanol in 15 ml of anhydrous dichloromethane was added at −15° C. 1.33 ml (9.52 mmol) of triethylamine and 0.74 ml (9.52 mmol) of methanesulfonyl chloride.

The resulting mixture was stirred at 0° C. for 1 h. The mixture was then diluted with water and dichloromethane and extracted with dichloromethane. Organic layer was dried and evaporated to give 1.73 g (88%) of methanesulfonic acid 6,7-dihydro-5H-cyclopentapyrazin-6-ylmethyl ester.

1.4 9-(6,7-Dihydro-5H-cyclopentapyrazin-6-ylmethyl)-7,7-dimethyl-2-(pyrimidin-4-yl)-6,7,8,9-tetrahydro-pyrimido[1,2-a]pyrimidin-4-one A suspension of 0.5 g (1.94 mmol) of 7,7-dimethyl-2-(pyrimidin-4-yl)-6,7,8,9-tetrahydro-4H-pyrimido[1,2-a]pyrimidin-4-one in 10 ml of anhydrous dimethylformamide was treated with 155 mg (3.89 mmol) of sodium hydride (50% suspension in mineral oil) and the resulting mixture was stirred for 40 min at 50° C. 0.888 g (3.89 mmol) of methanesulfonic acid 6,7-dihydro-5H-cyclopentapyrazin-6-ylmethyl ester in 2 ml of anhydrous dimethylformamide was added and the reaction mixture stirred at room temperature for 18 h. The solution was treated with water and extracted with ethyl acetate. The organic phase was dried and evaporated to give crude product, which was purified by silica gel chromatography, eluting with dichloromethane/methanol in the proportions 100/1 to 95/5 to give 80 mg of pure product obtained in the form of free base which was transformed into the hydrochloride salt. Mp: 193–195° C.

Example 2

Compound N° 11 of Table 1B

(+)-(6R)-9-(6,7-Dihydro-5H-[1]pyrindin-6-ylmethyl)-7,7-dimethyl-2-(pyrimidin-4-yl)-6,7,8,9-tetrahydro-pyrimido[1,2-a]pyrimidin-4-one

2.1 (−)-(6R,5R)-(6,7-Dihydro-5H-[1]pyrindin-6-yl)-(10,10-dimethyl-3,3-dioxa-3-thia-4-aza-tricyclo [5.2.1.0<1,5>]dec-4-yl]-methanone A suspension of 12 g (73.56 mmol) of (+/−)6,7-dihydro-5H-[1]pyrindine-6 Carboxylic acid (prepared by analogy to the method described in WO99/02517) in 85 ml of anhydrous dimethylformamide was treated with 13.36 g (82.39 mmol) of 1,1'-carbonyldiimidazole and the resulting mixture was heated at 45° C. for 1 h.

15.84 g (73.56 mmol) of (−)-10,2-camphorsultam (Fluka) and 11.2 g (73.56 mmol) of 1,8-diazabicyclo[5,4,0]undec-7-ene were added and the reaction mixture was stirred at 40° C. for 18 h.

The precipitate solid was recovered by filtration, washed with ethyl acetate, diethyl ether and dried affording 20.8 g (79%) of product as a white solid.

Mp.: 270–272° C. $[\alpha]_D^{20}$=−151° (c=1, CHCl$_3$).

2.2 (+)-(6R)-6,7-Dihydro-5H-[1]pyrindine-6-carboxylic acid

To a solution of 20.6 g (57.15 mmol) of (−)-(6R,5R)-(6, 7-dihydro-5H-[1]pyrindin-6-yl)-(10,10-dimethyl-3,3-dioxa-3-thia-4-aza-tricyclo[5.2.1.0<1,5>]dec-4-yl]-methanone in 300 ml of tetrahydrofuran/water in the proportions 2:1 was added 2.88 g (68.6 mmol) of lithium hydroxide. The mixture was allowed to stir at room temperature for 5 h. Water was added, and the reaction mixture was extracted with ethyl acetate. The aqueous phase was acidified to pH 6 with acetic acid. The precipitate obtained was filtered off and dried to give 7.5 g (81%) of white solid. Mp.: 236–237 $[\alpha]_D^{20}$=+5.4° (c=0.5, dimethylformamide).

2.3 (+)-(6R)-(6,7-Dihydro-5H-[1]pyrindin-6-yl)-methanol

To a solution of 3.26 g (20 mmol) of (+)-6,7-dihydro-5H-[1]pyrindine-6-carboxylic acid in 100 ml of anhydrous tetrahydrofuran under argon was added 1.14 g (30 mmol) of lithium aluminium hydride. The resulting mixture was stirred at room temperature for 1 h. Excess of lithium aluminium hydride was hydrolysed with 4.56 ml of water and 1.14 ml of sodium hydroxide (15%). The precipitate was filtered off and washed with diethyl ether, the filtrate was evaporated to give 2.88 g (97%) of product as an oil. $[\alpha]_D^{20}$=+6.2° (c=0.75, CH$_2$Cl$_2$).

2.4 Methanesulfonic acid 6,7-dihydro-5H-[1]pyrindin-6-ylmethyl ester

To a solution of 895 mg (6 mmol) of (+)-(6R)-(6,7-dihydro-5H-[1]pyrindin-6-yl)-methanol in 50 ml of anhydrous dichloromethane was added, at −15° C., 0.918 ml (6.6 mmol) of triethylamine and 0.465 ml (6 mmol) of methanesulfonyl chloride. The resulting mixture was stirred at 0° C. for 45 min. The mixture was then diluted with water and dichloromethane and extracted with dichloromethane. Organic layer was dried and evaporated to give 1.4 g (100%) of methanesulfonic acid 6,7-dihydro-5H-[1]pyrindin-6-ylmethyl ester.

2.5 (+)-(6R)-9-(6,7-Dihydro-5H-[1]pyrindine-ylmethyl)-7,7-dimethyl-2-(pyrimidin-4-yl)-6,7,8,9-tetrahydro-pyrimido[1,2-a]pyrimidin-4-one A suspension of 0.514 g (2 mmol) of 7,7-dimethyl-2-(pyrimidin-4-yl)-6,7,8,9-tetrahydro-4H-pyrimido[1,2-a]pyrimidin-4-one in 10 ml of anhydrous dimethylformamide was treated with 96 mg (2 mmol) of sodium hydride (50% suspension in mineral oil) and the resulting mixture was stirred for 40 min. 0.455 g (2 mmol) of methanesulfonic acid 6,7-dihydro-5H-[1]pyrindin-6-ylmethyl ester in 2 ml of anhydrous dimethylformamide was added and the reaction mixture stirred at room temperature for 18 h.

The solution was treated with water and extracted with ethyl acetate. The organic phase was dried and evaporated to give crude product, which was purified by silica gel chromatography, eluting with ethyl acetate/methanol/diethyl amine in the proportions 98/2/0.2 to give 0.338 g of pure product obtained in the form of free base. Mp: 156–185° C. $[\alpha]_D^{20}$=+13.6° (c=0.5, CH$_2$Cl$_2$).

Example 3

Compound N° 10 of Table 1B (−)-(6S)-9-(6,7-Dihydro-5H-[1]pyrindin-6-ylmethyl)-7,7-dimethyl-2-(pyrimidin-4-yl)-6,7,8,9-tetrahydro-pyrimido[1,2-a]pyrimidin-4-one By analogy with the method described in example 2, but replacing (−)-10,2-camphorsultam by the (+)-10,2-camphorsultam (Fluka), the compound was obtained as a free base. Mp.: 156–185° C. $[\alpha]_D^{20} = -14.1°$ (c=0.5, CH$_2$Cl$_2$).

Example 4

Compound N° 3 of Table 1B (+/−)9-(2-Chloro-6,7-dihydro-5H-[1]pyrindin-6-ylmethyl)-7,7-dimethyl-2-(pyrimidin-4-yl)-6,7,8,9-tetrahydro-pyrimido[1,2-a]pyrimidin-4-one

4.1 (+/−)(2-Chloro-6,7-dihydro-5H-[1]pyrindin-6-yl)-methanol

To a solution of 1.83 g (9.26 mmol) of (+/−)2-chloro-6,7-dihydro-5H-[1]pyrindine-6 carboxylic acid (prepared by analogy to the method described in WO99/02517) acid in 50 ml of anhydrous tetrahydrofuran under argon was added 0.52 g (13.89 mmol) of lithium aluminium hydride. The resulting mixture was stirred at room temperature for 2 h. Excess of lithium aluminium hydride was hydrolysed with 2.13 ml of water and 0.53 ml of sodium hydroxide (15%). The precipitate was filtered off and washed with diethyl ether, the filtrate was evaporated to give 1.61 g (95%) of product as an oil.

4.2 (+/−)Methanesulfonic acid 2-chloro-6,7-dihydro-5H-[1]pyrindin-6-yl-methyl ester The product was obtained by analogy with the method described in step 2.4 and using (+/−)(2-chloro-6,7-dihydro-5H-[1]pyrindin-6-yl)-methanol. The product was used as such in the next step.

4.3 (+/−)9-(2-Chloro-6,7-dihydro-5H-[1]pyrindin-6-ylmethyl)-7,7-dimethyl-2-(pyrimidin-4-yl)-6,7,8,9-tetrahydro-pyrimido[1,2-a]pyrimidin-4-one The product was obtained by analogy with the method described in step N° 2.5 using (+/−)Methanesulfonic acid 2-chloro-6,7-dihydro-5H-[1]pyrindin-6-yl-methyl ester in place of methanesulfonic acid 6,7-dihydro-5H-[1]pyrindin-6-ylmethyl ester. The compound was obtained in the form of free base. Mp: 186–187° C.

Example 5

Compound N° 2 of Table 1B (+/−)7,7-Dimethyl-2-(pyrimidin-4-yl)-9-(2-phenyl-6,7-dihydro-5H-[1]pyrindin-6-ylmethyl)-6,7,8,9-tetrahydro-pyrimido[1,2-a]pyrimidine-4-one A solution of 0.22 g (0.52 mmol) of (+/−)9-(2-chloro-6,7-dihydro-5H-[1]pyrindin-6-ylmethyl)-7,7-dimethyl-2-(pyrimidin-4-yl)-6,7,8,9-tetrahydro-pyrimido[1,2-a]pyrimidin-4-one in 3 ml of anhydrous toluene and 0.5 ml of ethanol was treated with 0.625 ml (2M solution in water) of sodium carbonate, 36 mg (0.03 mmol) of tetrakis(triphenylphosphine)palladium and 0.095 g (0.780 mmol) of phenylboronic acid. After being stirred for 24 h at 140° C., water was added, the mixture was extracted with dichlomethane. The organic phase was dried and evaporated to give crude product, which was purified by silica gel chromatography, eluting with dichloromethane/methanol/ammonia in the proportions 99/1/0.1 to give 0.133 g of pure product obtained in the form of free base. Mp: 209–211° C.

Example 6

Compound N° 4 of Table 1B (+/−)-9-(Chroman-3-ylmethyl)-7,7-dimethyl-2-(pyrimidin-4-yl)-6,7,8,9-tetrahydro-pyrimido[1,2-a]pyrimidin-4-one

6.1 (+/−)Methane sulfonic acid chroman-3-ylmethyl ester

The product was obtained by analogy with step N° 1.3 and using (+/−)chroman-3-yl-methanol (U.S. Pat. No. 4,957,928, Eur. J. Med. Chem., 1987, 22(6), 539–544). The compound was used as such in the next step.

6.2 (+/−)-9-Chroman-3-ylmethyl-7,7-dimethyl-2-(pyrimidin-4-yl)-6,7,8,9-tetrahydro-pyrimido[1,2-a]pyrimidin-4-one By analogy with the method described in step N° 1.4, using (+/−)methane sulfonic acid chroman-3-ylmethyl ester, the compound was obtained in the form of free base. Mp: 84–86° C.

Example 7

Compound N° 5 of Table 1B (+/−)-9-(6,7-Dihydro-5H-[2]pyrindin-6-ylmethyl)-7,7-dimethyl-2-(pyrimidin-4-yl)-6,7,8,9-tetrahydro-pyrimido[1,2-a]pyrimidin-4-one

7.1 (+/−)-(6,7-Dihydro-5H-[2]pyrindin-6-yl)-methanol

The product was obtained by analogy with step N° 1.2 and using (+/−)-6,7-Dihydro-5H-[2]pyrindine-6-carboxylic acid ethyl ester (prepared by analogy to the method described in WO99/02517) and was used as such in the next step.

7.2 (+/−)-Methanesulfonic acid 6,7-dihydro-5H-[2]pyrindin-6-ylmethyl ester

The product was obtained by analogy with step N° 1.3 using (+/−)-(6,7-dihydro-5H-[2]pyrindin-6-yl)-methanol from step N°è.1. The compound was used as such in the next step.

7.3 (+/−)-9-(6,7-Dihydro-5H-[2]pyrindin-6-ylmethyl)-7,7-dimethyl-2-(pyrimidin-4-yl)-6,7,8,9-tetrahydro-pyrimido[1,2-a]pyrimidin-4-one By analogy with the method described in step N° 1.4, using (+/−)-methanesulfonic acid 6,7-dihydro-5H-[2]pyrindin-6-ylmethyl ester, the compound was obtained in the form of free base. Mp: 169–171° C.

Example 8

Compound N° 6 of Table 1B (−)-(S)-9(2,3-Dihydro-benzofuran-2-ylmethyl)-7,7-dimethyl-2-(pyrimidin-4-yl)-6,7,8,9-tetrahydro-pyrimido[1,2-a]pyrimidin-4-one oxalate (1:1)

8.1 (−)-(S)-(2,3-Dihydro-benzofuran-2-yl) methanol

The product was obtained by analogy with step N° 1.2 and using (−)-(S)-2,3-dihydro-benzofuran-2-carboxylic acid (prepared by analogy to the method described in J. Med. Chem., 1983, 26(3), 328–334) and was used as such in the next step.

8.2 Methanesulfonic acid 2,3-dihydro-benzofuran-2-ylmethyl ester

The product was obtained by analogy with step N° 1.3, using (−)-(S)-(2,3-dihydro-benzofuran-2-yl)methanol from step N° 8.1, and was used as such in the next step.

8.3 (−)-(S)-9(2,3-Dihydro-benzofuran-2-ylmethyl)-7,7-dimethyl-2-(pyrimidin-4-yl)-6,7,8,9-tetrahydro-pyrimido[1,2-a]pyrimidin-4-one oxalate (1:1)

By analogy with the method described in step N° 1.4, using methanesulfonic acid 2,3-dihydro-benzofuran-2-ylmethyl ester, the compound was obtained in the form of free base which was transformed into the oxalate salt. Mp: 168–170° C. $[\alpha]_D^{20}=-1.4°$ (c=0.5, CH$_3$OH).

Example 9

Compound N° 7 of Table 1B (+/−)9-(5-Fluoro-8-methoxy-chroman-2-ylmethyl)-7,7-dimethyl-2-(pyrimidin-4-yl)-6,7,8,9-tetrahydro-pyrimido[1,2-a]pyrimidin-4-one 9.1 (+/−)(5-Fluoro-8-methoxy-3,4,4a,8a-tetrahydro-2H-chromen-2-yl)-methanol The product was obtained by analogy with step N° 1.2 and using (+/−)5-fluoro-8-methoxy-3,4,4a,8a-tetrahydro-2H-chromene-2-carboxylic acid ester (prepared by analogy to the method described in U.S. Pat. No. 5,137,901). The product was used as such in the next step.

9.2 (+/−)Methanesulfonic acid 5-fluoro-8-methoxy-3,4,4a,8a-tetrahydro-2H-chromen-2-ylmethyl ester The product was obtained by analogy with step N° 1.3 and using (+/−)(5-fluoro-8-methoxy-3,4,4a,8a-tetrahydro-2H-chromen-2-yl)-methanol from step N° 9.1. The product was used as such in the next step.

9.3 (+/−)9-(5-Fluoro-8-methoxy-chroman-2-ylmethyl)-7,7-dimethyl-2-(pyrimidin-4-yl)-6,7,8,9-tetrahydro-pyrimido[1,2-a]pyrimidin-4-one By analogy with the method described in step N° 1.4, using (+/−) methanesulfonic acid 5-fluoro-8-methoxy-3,4,4a,8a-tetrahydro-2H-chromen-2-ylmethyl ester, the compound was obtained in the form of free base. Mp: 136–138° C.

Example 10

Compound N° 8 of Table 1B (+/−)9-(2,3-dihydro-benzo[1,4]dioxin-2-ylmethyl)-7,7-dimethyl-2-(pyrimidin-4-yl)-6,7,8,9-tetrahydro-pyrimido[1,2-a]pyrimidin-4-one 10.1 (+/−)Methanesulfonic acid 2,3-dihydro-benzo[1,4]dioxin-2-ylmethyl ester The product was obtained by analogy with step N° 1.3 and using (+/−)-(2,3-dihydro-benzo[1,4]dioxin-2-yl)-methanol from Aldrich. The product was used as such in the next step.

10.2 (+/−)-9-(2,3-dihydro-benzo[1,4]dioxin-2-ylmethyl)-7,7-dimethyl-2-(pyrimidin-4-yl)-6,7,8,9-tetrahydro-pyrimido[1,2-a]pyrimidin-4-one By analogy with the method described in step N° 1.4, using (+/−) methanesulfonic acid 2,3-dihydro-benzodioxan-2-ylmethyl ester, the compound was obtained in the form of free base. Mp: 1.05–107° C.

Example 11

Compound N° 12 of Table 1B 9-(2-Furo[2,3-b]pyridin-3-yl-ethyl)-7,7-dimethyl-2-(pyrimidin-4-yl)-6,7,8,9-tetrahydro-pyrimido[1,2-a]pyrimidin-4-one hydrochloride (1:1)

11.1 Furo[2,3-b]pyridin-3-yl-acetic acid ethyl ester

To a suspension of 0.325 g (8.14 mmol) of sodium hydride (50% suspension in mineral oil) in 8 ml of anhydrous tetrahydrofuran was added 0.1 ml of 1,1,1,3,3,3-hexamethyldisilazane and 1.81 g (8.14 mmol) of triethyl phosphonoacetate (Aldrich) in 4 ml of anhydrous tetrahydrofuran. The resulting mixture was stirred at room temperature for 1 h, cooled at 0° C. and there was added 1 g (7.4 mmol) of furo[2,3-b]pyridin-3-one (prepared according to J. Het. Chem. 1986, 23, 1465–1469). After being stirred at room temperature for 24 h, water was added, the mixture was extracted with dichlomethane. The organic phase was dried and evaporated to give crude product, which was purified by silica gel chromatography, eluting with ethyl acetate/cyclohexane in the proportions 40/60 to give 0.73 g of pure product.

11.2 2-Furo[2,3-b]pyridin-3-yl-ethanol

The product was obtained by analogy with step N° 1.2 and using furo[2,3-b]pyridin-3-yl-acetic acid ethyl ester from step N° 11.1. The product was used as such in the next step.

11.3 Methanesulfonic acid 2-furo[2,3-b]pyridin-3-yl-ethyl ester

The product was obtained by analogy with step N° 1.3 and using 2-furo[2,3-b]pyridin-3-yl-ethanol from step N° 11.2. The product was used as such in the next step.

11.4 9-(2-Furo[2,3-b]pyridin-3-yl-ethyl)-7,7-dimethyl-2-(pyrimidin-4-yl)-6,7,8,9-tetrahydro-pyrimido[1,2-a]pyrimidin-4-one hydrochloride (1:1)

By analogy with the method described in step N° 1.4, using methanesulfonic acid 2-furo[2,3-b]pyridin-3-yl-ethyl ester, the compound was obtained in the form of free base which was transformed into the hydrochloride salt. Mp: 181–183° C.

Example 12

Compound N° 14 of table 1B

(+/−)-7,7-Dimethyl-9-(2-methyl-6,7-dihydro-5H-[1]pyrindin-6 ylmethyl)-2-(pyrimidin-4-yl)-6,7,8,9-tetrahydro-pyrimido[1,2-a]pyrimidin-4-one By analogy with the method described in example 1, using (+/−)(2-methyl-6,7-dihydro-5H-[1]pyrindin-6-yl)-methanol in place of (+/−)(2-chloro-6,7-dihydro-5H-[1]pyrindin-6-yl)-methanol, the compound was obtained as a free base.

Mp.: 163–164° C.

A list of chemical structures and physical data for compounds of the aforementioned formula (I), wherein R1 is a pyrimidine ring, illustrating the present invention is given in tables 1B and 2B. The compounds have been prepared according to the methods of the examples.

In the tables
(rac.) means racemic mixture,
(−) means levo isomer,
(+) means dextro isomer,
(R) means absolute R configuration and
(S) means absolute S configuration.

In the tables 1B and 2B, R1 is an unsubstituted 4-pyrimidine ring; in the column "X", when X represents two hydrogen atoms, only "H" is indicated; "m" and "p" equal 1.

TABLE 1B

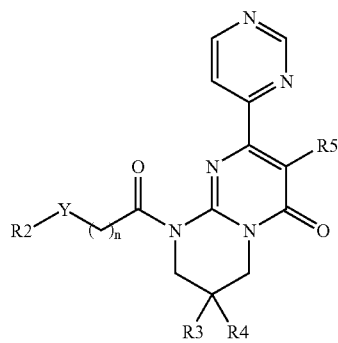

(I)

| N° | X | Y | R2 | R3 | R4 | R5 | n | Mp ° C. | salt |
|---|---|---|---|---|---|---|---|---|---|
| 1 | H | bond | (pyrindine-methyl) | CH₃ | CH₃ | H | 0 | 193–195 | Hydrochloride(1:1) |
| 2 | H | bond | (2-phenyl-pyrindine-methyl) (Rac.) | CH₃ | CH₃ | H | 0 | 209–211 | Free base |
| 3 | H | bond | (2-chloro-pyrindine-methyl) (Rac.) | CH₃ | CH₃ | H | 0 | 186–187 | Free base |
| 4 | H | bond | (chroman-3-ylmethyl) (Rac.) | CH₃ | CH₃ | H | 0 | 84–86 | Free base |

TABLE 1B-continued

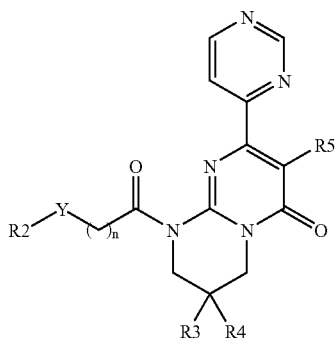

(I)

| N° | X | Y | R2 | R3 | R4 | R5 | n | Mp ° C. | salt |
|---|---|---|---|---|---|---|---|---|---|
| 5 | H | bond | ![](tetrahydrocyclopenta[c]pyridine) (Rac.) | CH₃ | CH₃ | H | 0 | 169–171 | Free base |
| 6 | H | bond | (−)-(S) | CH₃ | CH₃ | H | 0 | 168–170 | Oxalate(1:1) |
| 7 | H | bond | ![](8-OCH₃, 5-F chroman-2-yl) (Rac.) | CH₃ | CH₃ | H | 0 | 136–138 | Free base |
| 8 | H | bond | (Rac.) | CH₃ | CH₃ | H | 0 | 105–107 | Free base |
| 9 | H | bond | ![](5-OCH₃ chroman-2-yl) (Rac.) | CH₃ | CH₃ | H | 0 | 162–164 | Free base |
| 10 | H | bond | ![](tetrahydrocyclopenta[b]pyridine) (−)-(R) | CH₃ | CH₃ | H | 0 | 156–185 | Free base |
| 11 | H | bond | ![](tetrahydrocyclopenta[b]pyridine) (+)-(R) | CH₃ | CH₃ | H | 0 | 156–185 | Free base |

TABLE 1B-continued

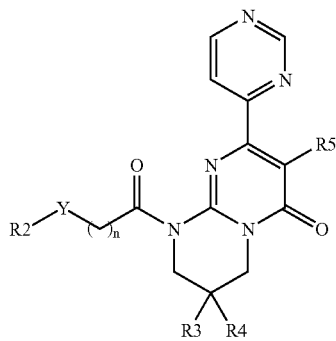
(I)

| N° | X | Y | R2 | R3 | R4 | R5 | n | Mp ° C. | salt |
|---|---|---|---|---|---|---|---|---|---|
| 12 | H | bond | 3-methyl-furo[2,3-b]pyridine | CH₃ | CH₃ | H | 1 | 181–183 | Hydrochloride(1:1) |
| 13 | H | bond | 2-methyl-benzofuran | CH₃ | CH₃ | H | 0 | 155–156 | Free base |
| 14 | H | bond | 2-methyl-6,7-dihydro-5H-cyclopenta[b]pyridine (Rac.) | CH₃ | CH₃ | H | 0 | 163–164 | Free base |

TABLE 2B

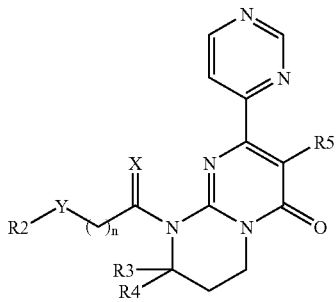
(I)

| N° | X | Y | R2 | R3 | R4 | R5 | n | Mp ° C. | salt |
|---|---|---|---|---|---|---|---|---|---|
| 1 | H | bond | 5-methoxy-3-methyl-2,3-dihydro-1,4-benzodioxine (Rac.) | H | CH₃(Rac.) | H | 0 | 173–175 | (1:1)Hydrochloride |
| 2 | H | bond | 3-methyl-2,3-dihydro-1,4-benzodioxine (Rac.) | CH₃ | CH₃ | H | 0 | 181–183 | Free base |

TABLE 2B-continued
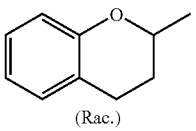
(I)
| N° | X | Y | R2 | R3 | R4 | R5 | n | Mp ° C. | salt |
|---|---|---|---|---|---|---|---|---|---|
| 3 | H | bond | 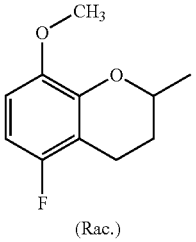 (Rac.) | H | CH₃(Rac.) | H | 0 | 117–119 | (1:1)Hydrochloride |
| 4 | H | bond | 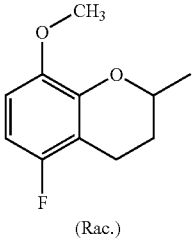 (Rac.) | H | CH₃(Rac.) | H | 0 | 211–213 | Free base |
| 5 | H | bond | 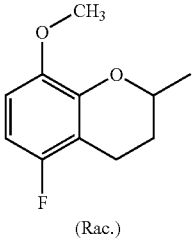 (Rac.) | CH₃ | CH₃ | H | 0 | 191–193 | Free base |
| 6 | H | bond | 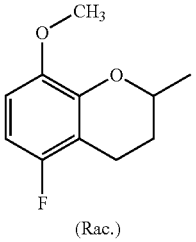 (Rac.) | CH₃ | CH₃ | H | 0 | 161–163 | Free base |
| 7 | H | bond | 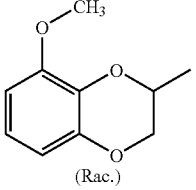 (Rac.) | CH₃ | CH₃ | H | 0 | 228–230 | Free base |
| 8 | H | bond | 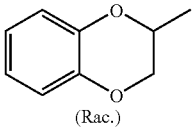 (Rac.) | H | CH₃(Rac.) | H | 0 | 159–161 | Free base |

TABLE 2B-continued (I)

| N° | X | Y | R2 | R3 | R4 | R5 | n | Mp ° C. | salt |
|----|---|---|----|----|----|----|---|---------|------|
| 9 | H | bond | 2,3-dihydro-1,4-benzodioxin-5-yl-methoxy (Rac.) | H | CH₃(Rac.) | H | 0 | 188–190 | Free base |
| 10 | H | bond | 2,3-dihydro-1,4-benzodioxin-5-yl-methoxy (Rac.) | CH₃ | CH₃ | H | 0 | 196–198 | Free base |
| 11 | H | Bond | 6,7-dihydro-5H-cyclopenta[b]pyridin-6-yl (R) | H | CH₃(Rac.) | H | 0 | 130–132 | Free base |
| 12 | H | Bond | 6,7-dihydro-5H-cyclopenta[b]pyridin-6-yl (R) | CH₃ | CH₃ | H | 0 | 160–162 | Free base |
| 13 | H | Bond | 6,7-dihydro-5H-cyclopenta[b]pyridin-6-yl (S) | CH₃ | CH₃ | H | 0 | 156–158 | Free base |
| 14 | H | Bond | furo[3,2-b]pyridin-2-yl | H | CH₃(Rac.) | H | 0 | 177–179 | Free base |
| 15 | H | Bond | 6,7-dihydro-5H-cyclopenta[b]pyridin-6-yl (S) | H | CH₃(Rac.) | H | 0 | 125–127 | Free base |
| 16 | H | Bond | 6,7-dihydro-5H-cyclopenta[c]pyridin-6-yl (Rac.) | H | CH₃(Rac.) | H | 0 | 161–163 | Free base |

Test Example

Inhibitory Activity of the Medicament of the Present Invention Against GSK3β

Two different protocols can be used.

In a first protocol: 7.5 µM of prephosphorylated GS1 peptide and 10 µM ATP (containing 300,000 cpm of 33P-ATP) were incubated in 25 mM Tris-HCl, pH 7.5, 0.6 mM DTT, 6 mM $MgCl_2$, 0.6 mM EGTA, 0.05 mg/ml BSA buffer for 1 hour at room temperature in the presence of GSK3β (total reaction volume: 100 microliters).

In a second protocol: 4.1 µM of prephosphorylated GS1 peptide and 42 µM ATP (containing 260,000 cpm 33P-ATP) were incubated in 80 mM Mes-NaOH, pH 6.5, 1 mM Mg acetate, 0.5 mM EGTA, 5 mM 2-mercaptoethanol, 0.02% Tween 20, 10% glycerol buffer for 2 hours at room temperature in the presence of GSK3β.

Inhibitors were solubilised in DMSO (final solvent concentration in the reaction medium, 1%).

The reaction was stopped with 100 microliters of a solution made of 25 g polyphosphoric acid (85% $P_2O_5$), 126 ml 85% $H_3PO_4$, $H_2O$ to 500 ml and then diluted to 1:100 before use. An aliquot of the reaction mixture was then transferred to Whatman P81 cation exchange filters and rinsed with the solution described above. Incorporated 33P radioactivity was determined by liquid scintillation spectrometry.

The phosphorylated GS-1 peptide had the following sequence: NH2-YRRAAVPPSPSLSRHSSPHQS(P)EDEE-COOH.

The GSK3β inhibitory activity of the compounds of the present invention are expressed in $IC_{50}$, and as an illustration the range of $IC_{50}$'s of the compounds:

in table 1A is between 5 nanomolar to 2 micromolar concentrations;

in table 2A is between 70 nanomolar to 2 micromolar concentrations;

in table 1B is between 5 nanomolar to 2 micromolar concentrations;

in table 2B is between 15 nanomolar to 2 micromolar concentrations.

As for example compound 4 of table 1A shows an $IC_{50}$ of 8 nM and compound 8 of table 2B an $IC_{50}$ of 15 nM.

Test Example 2

Inhibitory Activity of the Medicament of the Present Invention Against cdk5/p25

The following protocol may be used:

0.4 mg/ml Histone H1 and 10 µM ATP (containing 300,000 cpm of $^{33}$P-ATP) were incubated in 50 mM Hepes, pH 7.2, 1 mM DTT, 1 mM $MgCl_2$, 1 mM EGTA, 0.02% Tween 20 buffer for 1 hour at room temperature in the presence of cdk5/p25 (total reaction volume: 100 microliters).

Inhibitors were solubilised in DMSO (final solvent concentration in the reaction medium, 1%).

The reaction was stopped with 100 microliters of a solution of 25 g polyphosphoric acid (85% $P_2O_5$), 126 ml 85% $H_3PO_4$, $H_2O$ to 500 ml (diluted to 1:100 before use). An aliquot of the reaction mixture was then transferred to Whatman P81 cation exchange filters and rinsed with the solution described above. Incorporated $^{33}$P radioactivity was determined by liquid scintillation spectrometry.

The cdk5/p25 inhibitory activity of the compounds of the present invention are expressed as $IC_{50}$ values. Typically, 3-fold serial dilutions of the inhibitor over at least a 1000-fold concentration range are used.

As an illustration the range of $IC_{50}$'s of the compounds:

in table 1A is between 50 nanomolar to 2 micromolar concentrations;

in table 2A is >1 micromolar concentrations;

in table 1B is between 200 nanomolar to 5 micromolar;

in table 2B is >1 micromolar concentrations.

Formulation Example (1) Tablets

The ingredients below were mixed by an ordinary method and compressed by using a conventional apparatus.

| | |
|---|---|
| Compound of Example 1 | 30 mg |
| Crystalline cellulose | 60 mg |
| Corn starch | 100 mg |
| Lactose | 200 mg |
| Magnesium stearate | 4 mg |

(2) Soft Capsules

The ingredients below were mixed by an ordinary method and filled in soft capsules.

| | |
|---|---|
| Compound of Example 1 | 30 mg |
| Olive oil | 300 mg |
| Lecithin | 20 mg |

(1) Parenteral Preparations

The ingredients below were mixed by an ordinary method to prepare injections contained in a 1 ml ampoule.

| | |
|---|---|
| Compound of Example 1 | 3 mg |
| Sodium chloride | 4 mg |
| Distilled water for injection | 1 ml |

INDUSTRIAL APPLICABILITY

The compounds of the present invention have GSK3β or GSK3β and cdk5/p25 inhibitory activity and are useful as an active ingredient of a medicament for preventive and/or therapeutic treatment of diseases caused by abnormal activity of GSK3β or GSK3β and cdk5/p25 and more particularly of neurodegenerative diseases.

What is claimed is:

1. A compound of formula (I) or a salt thereof:

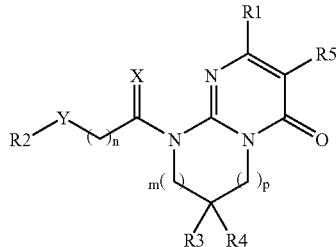

wherein:
- X represents two hydrogen atoms, a sulfur atom, an oxygen atom or a $C_{1-2}$ alkyl group and a hydrogen atom;
- Y represents a bond, an ethenylene group, an ethynylene group or a methylene group optionally substituted by one or two groups chosen from a $C_{1-6}$ alkyl group, a hydroxy group or a $C_{1-4}$ alkoxy group;
- R1 represents a 2, 3 or 4-pyridine ring or a 2, 4 or 5-pyrimidine ring, the ring being optionally substituted by a $C_{3-6}$ cycloalkyl group, a $C_{1-4}$ alkyl group, a $C_{1-4}$ alkoxy group, a benzyl group or a halogen atom;
- R2 represents a heterocyclic bicyclic ring having 1–4 heteroatoms selected from an oxygen atom, a sulfur atom and a nitrogen atom and having 5–9 carbon atoms, of formula

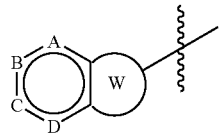

wherein A, B, C and D represent, each independently, a carbon atom or a nitrogen atom and W represent a saturated or unsaturated 5, 6 or 7 membered cyclic ring having from 3 to 7 carbon atoms and 2 to 0 heteroatoms selected from an oxygen atom, a sulfur atom or a nitrogen atom; the R2 group being optionally substituted on a carbon atom or, when possible, on a nitrogen atom by one or two atoms or groups chosen from a halogen atom, a $C_{1-6}$ alkyl group, a hydroxy group, a $C_{1-4}$ alkoxy group, a benzene ring, a pyridine ring or a —NR6R7 group;
- R3 represents a hydrogen atom, a $C_{1-6}$ alkyl group, a hydroxy group, a $C_{1-4}$ alkoxy group or a halogen atom;
- R4 represents a hydrogen atom, a $C_{1-6}$ alkyl group, a $C_{1-4}$ alkoxy group or a halogen atom;
- R5 represents a hydrogen atom, a $C_{1-6}$ alkyl group, a $C_{1-2}$ perhalogenated alkyl group, a $C_{1-3}$ halogenated alkyl group or a halogen atom;
- R6 and R7 represent, each independently, a hydrogen atom, a $C_{1-6}$ alkyl group, a benzyl group, a benzene ring or R6 and R7 represent together with the nitrogen atom, a pyrrolidine ring, a piperidine ring, a hexamethyleneimine ring, a morpholine ring or a piperazine ring, the ring being optionally substituted by one or two $C_{1-6}$ alkyl group;
- when m equals 0, p equals 1, 2 or 3,
- when m equals 1, p equals 0, 1 or 2,
- when m equals 2, p equals 0 or 1;
- when m equals 3, p equals 0;
- and
- n represents 0 to 3;

with the proviso that the compound of formula (I) is not:
- 9-[2-(1H-indol-3-yl)ethyl]-2-pyridin-4-yl-6,7,8,9-tetrahydro-4H-pyrimido[1,2-a]pyrimidin-4-one;
- 9-[3-(1H-indol-3-yl)propyl]-2-pyridin-4-yl-6,7,8,9-tetrahydro-4H-pyrimido[1,2-a]pyrimidin-4-one;
- 1-[2-(1H-Indol-3-yl)ethyl]-7-pyridin-4-yl-2,3-dihydroimidazo[1,2-a]pyrimidin-5(1H)-one, or
- 1-[3-(1H-indol-3-yl)propyl]-7-pyridin-4-yl-2,3-dihydroimidazo[1,2-a]pyrimidin-5(1H)-one.

2. The compound according to claim 1, wherein R1 represents an unsubstituted pyridinyl group or an unsubstituted 4-pyrimidine ring.

3. A compound selected from the group consisting of:
- (+)-(6R)-9-(6,7-dihydro-5H-[1]pyrindin-6-ylmethyl)-7,7-dimethyl-2-(pyridin-4-yl)-6,7,8,9-tetrahydro-pyrimido[1,2-a]pyrimidin-4-one
- (−)-(6S)-9-(6,7-dihydro-5H-[1]pyrindin-6-ylmethyl)-7,7-dimethyl-2-(pyridin-4-yl)-6,7,8,9-tetrahydro-pyrimido[1,2-a]pyrimidin-4-one
- (+)-(6R)-9-(6,7-dihydro-5H-[1]pyrindin-6-ylmethyl)-2-(pyridin-4-yl)-6,7,8,9-tetrahydro-pyrimido[1,2-a]pyrimidin-4-one
- (+/−)-7,7-dimethyl-9-(2-methyl-6,7-dihydro-5H-[1]pyrindin-6-ylmethyl)-2-(pyridin -4-yl)-6,7,8,9-tetrahydro-pyrimido[1,2-a]pyrimidin-4-one.
- (+)-7,7-dimethyl-9-(2-methyl-6,7-dihydro-5H-[1]pyrindin-6-ylmethyl)-2-(pyridin-4 -yl)-6,7,8,9-tetrahydro-pyrimido[1,2-a]pyrimidin-4-one
- (−)-7,7-dimethyl-9-(2-methyl-6,7-dihydro-5H-[1]-pyrindin-6-ylmethyl)-2-(pyridin-4 yl)-6,7,8,9-tetrahydro-pyrimido[1,2-a]pyrimidin-4-one
- (+/−)-9-(2,3-dihydro-benzofuran-2-ylmethyl)-7,7-dimethyl-2-(pyridin-4-yl)-6,7,8,9-tetrahydro-pyrimido[1,2-a]pyrimidin-4-one
- 9-(furo[3,2-b]pyridin-2-ylmethyl)-7,7-dimethyl-2-(pyridin-4-yl)-6,7,8,9-tetrahydro-pyrimido[1,2-a]pyrimidin-4-one
- 9-(benzofuran-2-ylmethyl)-7,7-dimethyl-2-(pyridin-4-yl)-6,7,8,9-tetrahydro-pyrimido[1,2-a]pyrimidin-4-one
- (+/−)9-(2-chloro-6,7-dihydro-5H-[1]pyrindin-6-ylmethyl)-7,7-dimethyl-2-(pyridin -4-yl)-6,7,8,9-tetrahydro-pyrimido[1,2-a]pyrimidin-4-one
- (+/−)7,7-dimethyl-2-(pyridin-4-yl)-9-[2-(pyridin-4-yl)-6,7-dihydro-5H-[1]pyrindin-6-ylmethyl]-6,7,8,9-tetrahydro-pyrimido[1,2-a]pyrimidine-4-one
- (+/−)7,7-dimethyl-9-(2-phenyl-6,7-dihydro-5H-[1]pyrindin-6-ylmethyl)-2-(pyridin -4-yl)-6,7,8,9-tetrahydro-pyrimido[1,2-a]pyrimidine-4-one
- (+/−)7,7-dimethyl-2-(pyridin-4-yl)-9-[2-(pyrrolidin-1-yl)-6,7-dihydro-5H-[1]pyrindin-6-ylmethyl]-6,7,8,9-tetrahydro-pyrimido[1,2-a]pyrimidin-4-one
- (+/−)7,7-difluoro-9-(2-methyl-6,7-dihydro-5H-[1]pyrindin-6-ylmethyl)-2-(pyridin-4-yl)-6,7,8,9-tetrahydro-pyrimido[1,2-a]pyrimidine-4-one
- 9-((+)-(6-R)-6,7-dihydro-5H-[1]pyrindin-6-ylmethyl)-(+/−)-7-methyl-2-(pyridin-4-yl)-6,7,8,9-tetrahydro-pyrimido[1,2-a]pyrimidine-4-one or a salt thereof.

4. A method for the treatment of non-insulin dependent diabetes; which comprises administering to a patient in need of said treatment an effective amount of a compound according to claim 1.

5. A compound selected from the group consisting of:
9-chroman-2-ylmethyl-8-methyl-2-pyridin-4-yl-6,7,8,9-tetrahydro-pyrimido[1,2-a]pyrimidin-4-one
9-(8-methoxy-2,3-dihydro-benzo[1,4]dioxin-2-ylmethyl)-8-methyl-2-pyridin-4-yl-6,7,8,9-tetrahydro-pyrimido[1,2-a]pyrimidin-4-one
9-(2,3-dihydro-benzo[1,4]dioxin-2-ylmethyl)-8-methyl-2-pyridin-4-yl-6,7,8,9-tetrahydro-pyrimido[1,2-a]pyrimidin-4-one
9-(5-methoxy-2,3-dihydro-benzo[1,4]dioxin-2-ylmethyl)-8-methyl-2-pyridin-4-yl-6,7,8,9-tetrahydro-pyrimido[1,2-a]pyrimidin-4-one
9-(6,7-dihydro-5H-[1]pyrindin-6-(R)-ylmethyl)-8,8-dimethyl-2-pyridin-4-yl-6,7,8,9-tetrahydro-pyrimido[1,2-a]pyrimidin-4-one
9-chroman-2-ylmethyl-8,8-dimethyl-2-pyridin-4-yl-6,7,8,9-tetrahydro-pyrimido[1,2-a]pyrimidin-4-one
9-(2,3-dihydro-benzo[1,4]dioxin-2-ylmethyl)-8,8-dimethyl-2-pyridin-4-yl-6,7,8,9-tetrahydro-pyrimido[1,2-a]pyrimidin-4-one
9-(5-fluoro-8-methoxy-chroman-2-ylmethyl)-8,8-dimethyl-2-pyridin-4-yl-6,7,8,9-tetrahydro-pyrimido[1,2-a]pyrimidin-4-one
9-furo[3,2-b]pyridin-2-ylmethyl-8-methyl-2-pyridin-4-yl-6,7,8,9-tetrahydro-pyrimido[1,2-a]pyrimidin-4-one
9-(6,7-dihydro-5H-[1]pyrindin-6-(R)-ylmethyl)-8-methyl-2-pyridin-4-yl-6,7,8,9-tetrahydro-pyrimido[1,2-a]pyrimidin-4-one
9-(6,7-dihydro-5H-[2]pyrindin-6-ylmethyl)-8-methyl-2-pyridin-4-yl-6,7,8,9-tetrahydro-pyrimido[1,2-a]pyrimidin-4-one
9-(6,7-dihydro-5H-[1]pyrindin-6-(S)-ylmethyl)-8-methyl-2-pyridin-4-yl-6,7,8,9-tetrahydro-pyrimido[1,2-a]pyrimidin-4-one
or a salt thereof.

6. A compound selected from the group consisting of:
9-(6,7-dihydro-5H-cyclopentapyrazin-6-ylmethyl)-7,7-dimethyl-2-pyrimidin-4-yl-6,7,8,9-tetrahydro-pyrimido[1,2-a]pyrimidin-4-one
(+/−)7,7-dimethyl-2-(pyrimidin-4-yl)-9-(2-phenyl-6,7-dihydro-5H-[1]pyrindin-6 -ylmethyl)-6,7,8,9-tetrahydro-pyrimido[1,2-a]pyrimidine-4-one
(+/−)9-(2-chloro-6,7-dihydro-5H-[1]pyrindin-6-ylmethyl)-7,7-dimethyl-2-(pyrimidin -4-yl)-6,7,8,9-tetrahydro-pyrimido[1,2-a]pyrimidin-4-one
(+/−)-9-(chroman-3-ylmethyl)-7,7-dimethyl-2-(pyrimidin-4-yl)-6,7,8,9-tetrahydro-pyrimido[1,2-a]pyrimidin-4-one
(+/−)-9-(6,7-dihydro-5H-[2]pyrindin-6-ylmethyl)-7,7-dimethyl-2-(pyrimidin-4-yl) -6,7,8,9-tetrahydro-pyrimido[1,2-a]pyrimidin-4-one
(−)-(S)-9-(2,3-dihydro-benzofuran-2-ylmethyl)-7,7-dimethyl-2-(pyrimidin-4-yl)-6,7,8,9-tetrahydro-pyrimido[1,2-a]pyrimidin-4-one
(+/−)9-(5-fluoro-8-methoxy-chroman-2-ylmethyl)-7,7-dimethyl-2-(pyrimidin-4-yl)-6,7,8,9-tetrahydro-pyrimido[1,2-a]pyrimidin-4-one
(+/−)9-(2,3-dihydro-benzo[1,4]dioxin-2-ylmethyl)-7,7-dimethyl-2-(pyrimidin-4-yl)-6,7,8,9-tetrahydro-pyrimido[1,2-a]pyrimidin-4-one
(+/−)-9-(5-methoxy-2,3-dihydro-benzo[1,4]dioxin-2-ylmethyl)-7,7-dimethyl-2-(pyrimidin-4-yl)-6,7,8,9-tetrahydro-pyrimido[1,2-a]pyrimidin-4-one
(−)-(6S)-9-(6,7-dihydro-5H-[1]pyrindin-6-ylmethyl)-7,7-dimethyl-2-(pyrimidin-4-yl)-6,7,8,9-tetrahydro-pyrimido[1,2-a]pyrimidin-4-one
(+)-(6R)-9-(6,7-dihydro-5H-[1]pyrindin-6-ylmethyl)-7,7-dimethyl-2-(pyrimidin-4-yl)-6,7,8,9-tetrahydro-pyrimido[1,2-a]pyrimidin-4-one
9-(2-furo[2,3-b]pyridin-3-yl-ethyl)-7,7-dimethyl-2-(pyrimidin-4-yl)-6,7,8,9-tetrahydro-pyrimido[1,2-a]pyrimidin-4-one
9-benzofuran-2-ylmethyl-7,7-dimethyl-2-(pyrimidin-4-yl)-6,7,8,9-tetrahydro-pyrimido[1,2-a]pyrimidin-4-one
(+/−)-7,7-dimethyl-9-(2-methyl-6,7-dihydro-5H-[1]pyrindin-6 ylmethyl)-2-(pyrimidin-4-yl)-6,7,8,9,-tetrahydro-pyrimido[1,2-a]pyrimidin-4-one
or a salt thereof.

7. A compound selected from the group consisting of:
9-(8-methoxy-2,3-dihydro-benzo[1,4]dioxin-2-ylmethyl)-8-methyl-2-pyrimidin-4-yl-6,7,8,9-tetrahydro-pyrimido[1,2-a]pyrimidin-4-one
9-(2,3-dihydro-benzo[1,4]dioxin-2-ylmethyl)-8,8-dimethyl-2-pyrimidin-4-yl-6,7,8,9-tetrahydro-pyrimido[1,2-a]pyrimidin-4-one
9-chroman-2-ylmethyl-8-methyl-2-pyrimidin-4-yl-6,7,8,9-tetrahydro-pyrimido[1,2-a]pyrimidin-4-one
9-(5-fluoro-8-methoxy-chroman-2-ylmethyl)-8-methyl-2-pyrimidin-4-yl-6,7,8,9-tetrahydro-pyrimido[1,2-a]pyrimidin-4-one
9-(5-fluoro-8-methoxy-chroman-2-ylmethyl)-8,8-dimethyl-2-pyrimidin-4-yl-6,7,8,9-tetrahydro-pyrimido[1,2-a]pyrimidin-4-one
9-chroman-2-ylmethyl-8,8-dimethyl-2-pyrimidin-4-yl-6,7,8,9-tetrahydro-pyrimido[1,2-a]pyrimidin-4-one
9-(8-methoxy-2,3-dihydro-benzo[1,4]dioxin-2-ylmethyl)-8,8-dimethyl-2-pyrimidin-4-yl-6,7,8,9-tetrahydro-pyrimido[1,2-a]pyrimidin-4-one
9-(2,3-dihydro-benzo[1,4]dioxin-2-ylmethyl)-8-methyl-2-pyrimidin-4-yl-6,7,8,9-tetrahydro-pyrimido[1,2-a]pyrimidin-4-one
9-(5-methoxy-2,3-dihydro-benzo[1,4]dioxin-2-ylmethyl)-8-methyl-2-pyrimidin-4-yl-6,7,8,9-tetrahydro-pyrimido[1,2-a]pyrimidin-4-one
9-(5-methoxy-2,3-dihydro-benzo[1,4]dioxin-2-ylmethyl)-8,8-dimethyl-2-pyrimidin-4-yl-6,7,8,9-tetrahydro-pyrimido[1,2-a]pyrimidin-4-one
9-(6,7-dihydro-5H-[1]pyrindin-6-(R)-ylmethyl)-8-methyl-2-pyrimidin-4-yl-6,7,8,9-tetrahydro-pyrimido[1,2-a]pyrimidin-4-one
9-(6,7-dihydro-5H-[1]pyrindin-6-(R)-ylmethyl)-8,8-dimethyl-2-pyrimidin-4-yl-6,7,8,9 -tetrahydro-pyrimido[1,2-a]pyrimidin-4-one
9-(6,7-dihydro-5H-[1]pyrindin-6-(S)-ylmethyl)-8,8-dimethyl-2-pyrimidin-4-yl-6,7,8,9 -tetrahydro-pyrimido[1,2-a]pyrimidin-4-one
9-furo[3,2-b]pyridin-2-ylmethyl-8-methyl-2-pyrimidin-4-yl-6,7,8,9-tetrahydro-pyrimido[1,2-a]pyrimidin-4-one
9-(6,7-dihydro-5H-[1]pyrindin-6-(S)-ylmethyl)-8-methyl-2-pyrimidin-4-yl-6,7,8,9-tetrahydro-pyrimido[1,2-a]pyrimidin-4-one or
9-(6,7-dihydro-5H-[2]pyrindin-6-ylmethyl)-8-methyl-2-pyrimidin-4-yl-6,7,8,9-tetrahydro-pyrimido[1,2-a]pyrimidin-4-one
or a salt thereof.

8. A method for the treatment of non-insulin dependent diabetes; which comprises administering to a patient in need of said treatment an effective amount of a compound according to claim 2.

9. A method for the treatment of non-insulin dependent diabetes; which comprises administering to a patient in need of said treatment an effective amount of a compound according to claim 3.

10. A method for the treatment of non-insulin dependent diabetes; which comprises administering to a patient in need of said treatment an effective amount of a compound according to claim 5.

11. A method for the treatment of non-insulin dependent diabetes; which comprises administering to a patient in need of said treatment an effective amount of a compound according to claim 6.

12. A method for the treatment of non-insulin dependent diabetes; which comprises administering to a patient in need of said treatment an effective amount of a compound according to claim 7.

* * * * *